(12) United States Patent
Cooks et al.

(10) Patent No.: US 10,213,143 B2
(45) Date of Patent: *Feb. 26, 2019

(54) ENCLOSED DESORPTION ELECTROSPRAY IONIZATION PROBES AND METHOD OF USE THEREOF

(71) Applicant: Purdue Research Foundation, West Lafayette, IN (US)

(72) Inventors: Robert Graham Cooks, West Lafayette, IN (US); Zheng Ouyang, West Lafayette, IN (US); Chien-Hsun Chen, West Lafayette, IN (US); Ziqing Lin, West Lafayette, IN (US); Livia Schiavinato Eberlin, Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/989,706

(22) Filed: May 25, 2018

(65) Prior Publication Data

US 2018/0279927 A1    Oct. 4, 2018

Related U.S. Application Data

(63) Continuation of application No. 15/617,013, filed on Jun. 8, 2017, now Pat. No. 10,004,440, which is a
(Continued)

(51) Int. Cl.
*H01J 49/00* (2006.01)
*A61B 5/1477* (2006.01)
(Continued)

(52) U.S. Cl.
CPC ........ *A61B 5/1477* (2013.01); *A61B 10/0045* (2013.01); *A61M 11/00* (2013.01);
(Continued)

(58) Field of Classification Search
CPC ........ H01J 49/00; H01J 49/0009; H01J 49/04; H01J 49/0409; H01J 49/0459; H01J 49/0468; H01J 49/0489; H01J 49/0463
(Continued)

(56) References Cited

U.S. PATENT DOCUMENTS 4,187,856 A    2/1980  Hall et al.
4,787,856 A   11/1988  Chazin
(Continued)

OTHER PUBLICATIONS

Chace, D. H., "Mass Spectrometry in the Clinical Laboratory" Chem. Rev. 2001, 101, 445-477.
(Continued)

*Primary Examiner* — Jason McCormack
(74) *Attorney, Agent, or Firm* — Brown Rudnick LLP; Adam M. Schoen

(57) ABSTRACT

The invention generally relates to enclosed desorption electrospray ionization probes, systems, and methods. In certain embodiments, the invention provides a source of DESI-active spray, in which a distal portion of the source is enclosed within a transfer member such that the DESI-active spray is produced within the transfer member.

20 Claims, 19 Drawing Sheets

Related U.S. Application Data continuation of application No. 15/400,358, filed on Jan. 6, 2017, now Pat. No. 9,700,251, which is a continuation of application No. 14/688,496, filed on Apr. 16, 2015, now Pat. No. 9,538,945, which is a continuation of application No. 13/486,824, filed on Jun. 1, 2012, now Pat. No. 9,024,254.

(60) Provisional application No. 61/492,948, filed on Jun. 3, 2011.

(51) Int. Cl.
| | |
|---|---|
| G01N 33/483 | (2006.01) |
| H01J 49/34 | (2006.01) |
| A61M 11/00 | (2006.01) |
| A61M 25/00 | (2006.01) |
| H01J 49/04 | (2006.01) |
| H01J 49/16 | (2006.01) |
| A61B 10/00 | (2006.01) |
| A61B 5/15 | (2006.01) |
| G01N 1/02 | (2006.01) |
| A61B 5/157 | (2006.01) |
| A61B 5/145 | (2006.01) |

(52) U.S. Cl.
CPC ......... *A61M 25/00* (2013.01); *G01N 33/4833* (2013.01); *H01J 49/0022* (2013.01); *H01J 49/0404* (2013.01); *H01J 49/0445* (2013.01); *H01J 49/167* (2013.01); *H01J 49/34* (2013.01); *A61B 5/1405* (2013.01); *A61B 5/145* (2013.01); *A61B 5/157* (2013.01); *A61B 5/150015* (2013.01); *A61B 5/150992* (2013.01); *A61M 2202/0468* (2013.01); *G01N 2001/028* (2013.01)

(58) Field of Classification Search
USPC ............... 250/281, 282, 283, 284, 288, 289
See application file for complete search history.

(56) References Cited

U.S. PATENT DOCUMENTS

| | | | |
|---|---|---|---|
| 6,803,566 B2 | 10/2004 | Van Berkel | |
| 7,335,897 B2 | 2/2008 | Takats et al. | |
| 8,063,362 B1 | 11/2011 | Dressler et al. | |
| 8,421,005 B2 | 4/2013 | Musselman | |
| 9,024,254 B2 | 5/2015 | Cooks et al. | |
| 9,538,945 B2 | 1/2017 | Cooks et al. | |
| 9,700,251 B2* | 7/2017 | Cooks ............... | A61B 10/0045 |
| 10,004,440 B2* | 6/2018 | Cooks ............... | A61B 10/0045 |
| 2005/0230635 A1 | 10/2005 | Takats et al. | |
| 2008/0156985 A1 | 7/2008 | Venter et al. | |
| 2009/0272890 A1 | 11/2009 | Ogawa et al. | |
| 2009/0302211 A1* | 12/2009 | Takats ............... | G01N 1/286 |
| | | | 435/30 |
| 2010/0140468 A1 | 6/2010 | Musselman | |
| 2010/0258717 A1* | 10/2010 | Chen .................. | H01J 49/0431 |
| | | | 250/288 |
| 2010/0301209 A1 | 12/2010 | Ouyang et al. | |
| 2011/0084203 A1 | 4/2011 | Basile et al. | |
| 2011/0220784 A1 | 9/2011 | Roach et al. | |
| 2011/0240844 A1 | 10/2011 | Ouyang et al. | |

OTHER PUBLICATIONS

Cooks, R. G.; et al., "Ambient Mass Spectrometry"., Science 2006, 311, 1566-1570.
Garimella, S., et al. "Gas-flow assisted ion transfer for mass spectrometry", Journal of mass spectrometry: JMS 2012, 47, 201-7.
Girod, M. et al. "Desorption Electrospray Ionization Imaging Mass Spectrometry of Lipids in Rat Spinal Cord" J. Am. Soc. Mass Spectrom.2010, 21, 1177-1189.
Green, F. M., et al. "The effect of electrospray solvent composition on desorption electrospray ionisation (DESI) efficiency and spatial resolution", Analyst 2010, 135, 731-737.
Haddad et al., Desorption Sonic Spray Ionization for (high) Voltage Free Ambient Mass Spectrometry, 2006, Rapid Communications in Mass Spectrometry, 20, 2901-2905.
Hu et al., "The Orbitrap: a new mass spectrometer" J. Mass. Spectrom., 40:430-433, 2005.
Ifa et al., Desorption Electrospray Ioinzation and Other Ambient Ionization Methods: current Progress and Preview, Mar. 2, 2010, Royal Society of Chemistry, Analyst, 135, 669-681.
Nemes, P. et al. "Simultaneous Imaging of Small Metabolites and Lipids in Rat Brain Tissues at Atmospheric Pressure by Laser Ablation Electrospray Ionization Mass Spectrometry", Anal. Chem. 2010, 82, 982-988.
Scamman et al., Frequency Response of Long Mass-Spectrometer Sampling Catheters, 1986, Anesthesiology, 65, 422-435.
Schwartz, J. C. et al. "A Two-Dimensional Quadrupole Ion Trap Mass Spectrometer"., J. Am. Soc. Mass Spectrom, 2002, 13, 659-669.
Takats, Z. et al. "Mass Spectrometry Sampling Under Ambient Conditions with Desorption Electrospray Ionization", J. Mass Spectrom. 2005, 40, 1261-1275.
Wang, H.; et al. "Direct Analysis of Biological Tissue by Paper Spray Mass Spectrometry"., Anal. Chem. 2011, 83, 1197-1201.
Wells, J. M. et al. "A Quadrupole Ion Trap with Cylindrical Geometry Operated in the Mass-Selective Instability Mode", Anal. Chem., 1998, 70, 438-444.
Wiseman, J. M. et al. "Mass Spectrometric Profiling of Intact Biological Tissue by Using Desorption Electrospray Ionization" Angew. Chem.-Int. Edit. 2005, 44, 7094-7097.
Yu et al., Direct Profiling of Phytochemicals in Tulip Tissues and in Vivo Monitoring of the Change of Carbohydrate Content in Tulip Bulbs by Probe Electrospray Ionization Mass Spectrometry, J AM Soc Mass Spectrom, 2009, 20, 2304-2311.
Chen et al., Neutral Desorption Sampling of Biological Surfaces for Rapid Chemical Characterization by Extractive Electrospray Ionization Mass Spectrometry, Natur Publishing Group, Aug. 28 2008, pp. 1467-1475.

\* cited by examiner

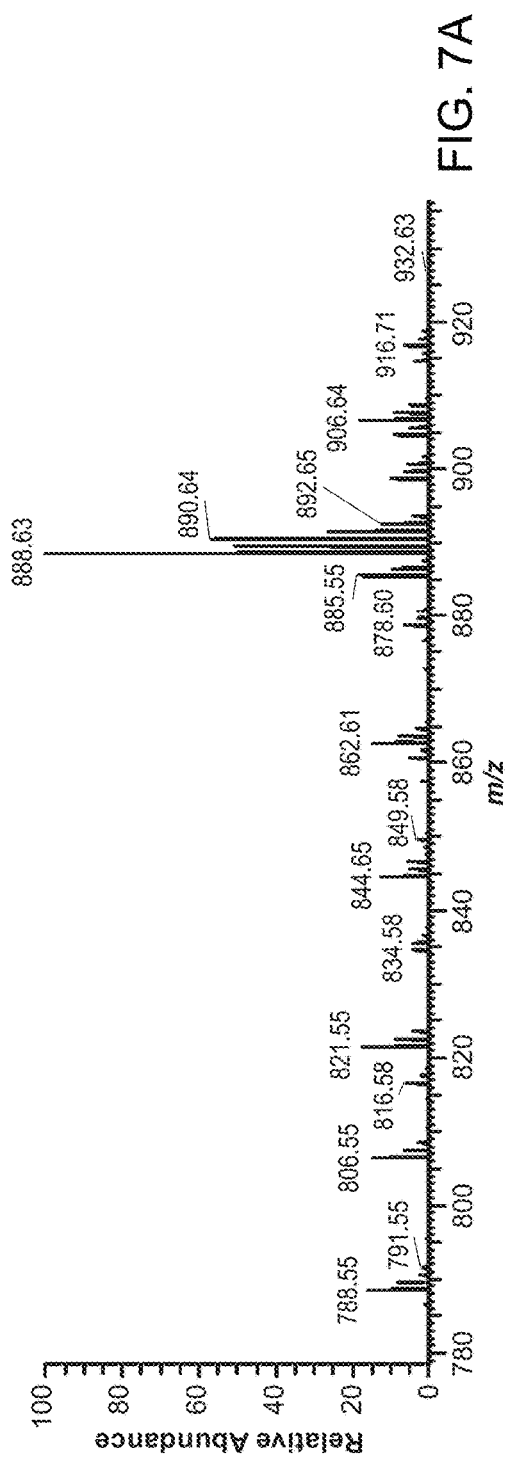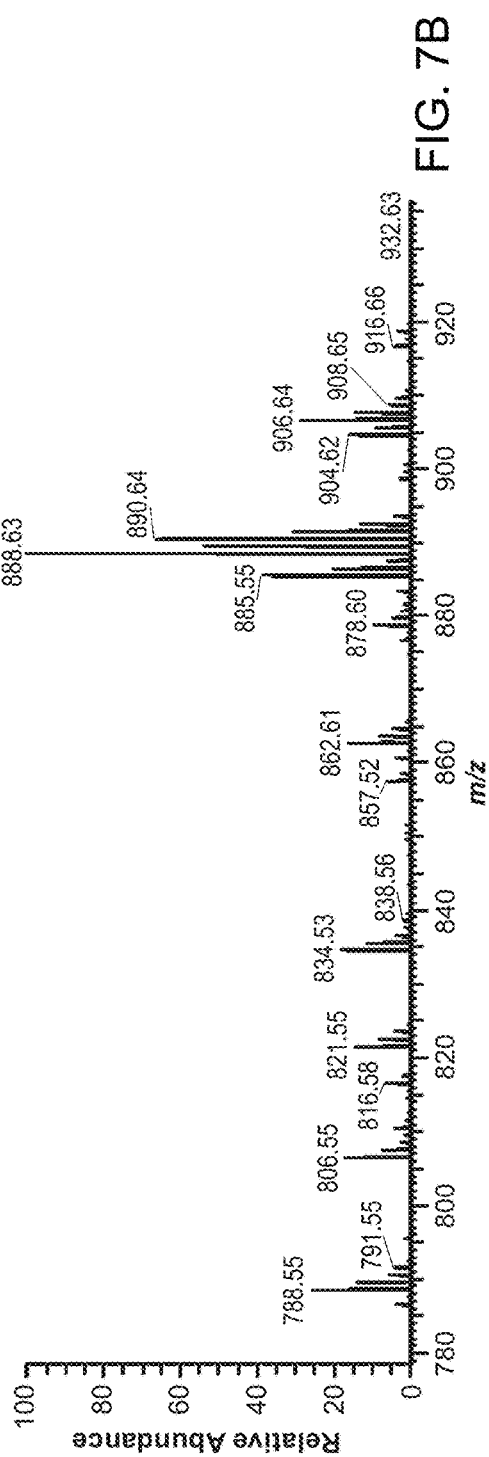

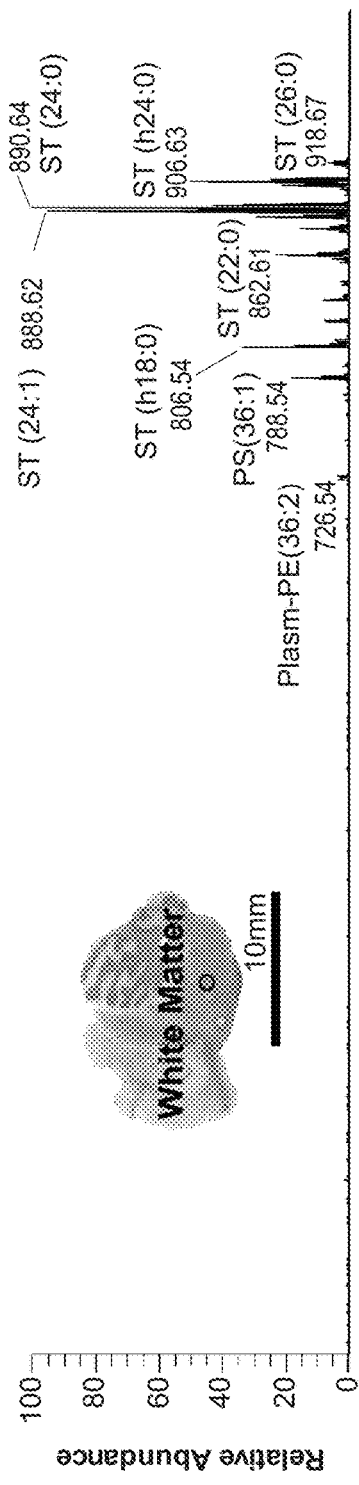
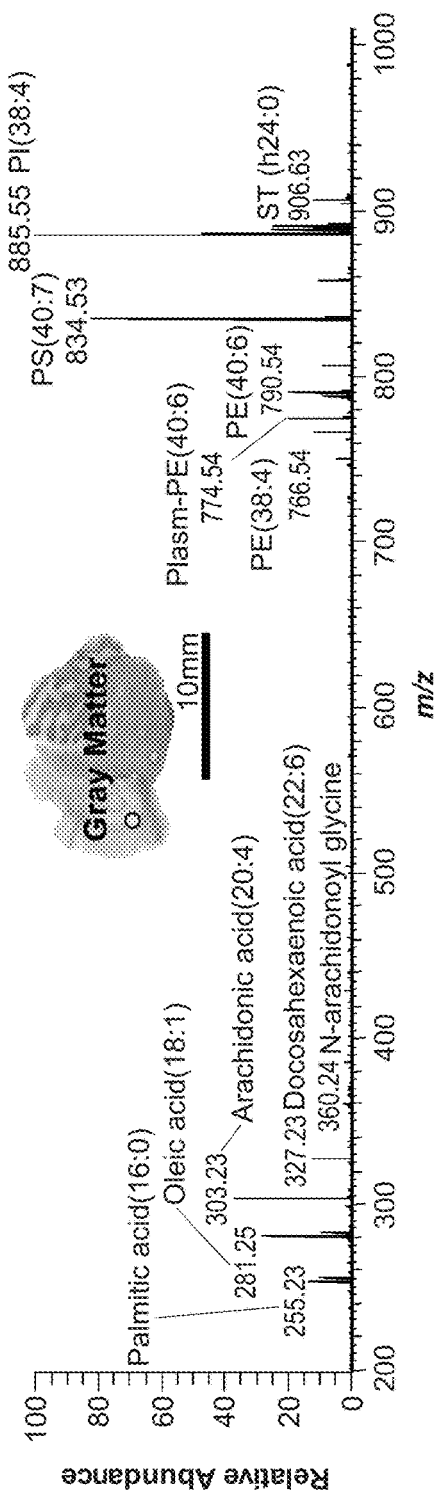

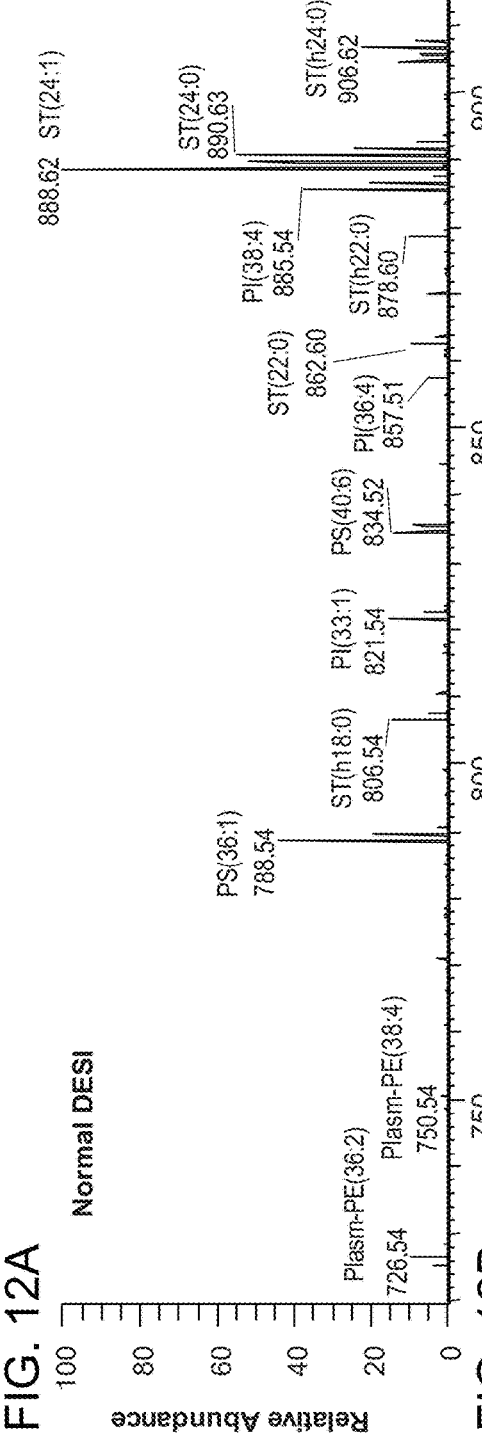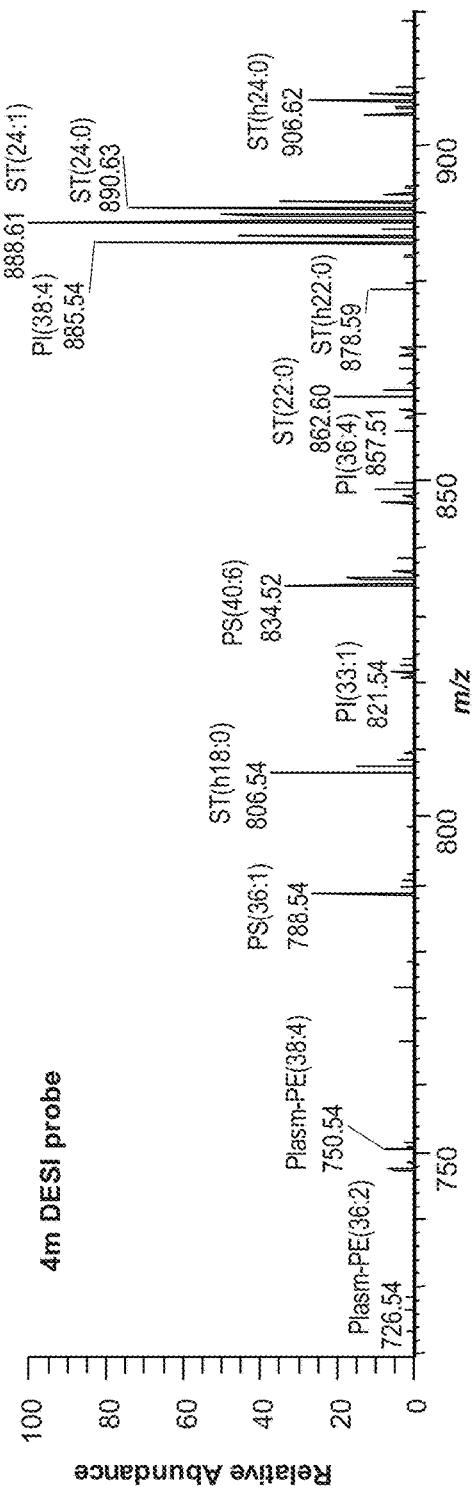

ENCLOSED DESORPTION ELECTROSPRAY IONIZATION PROBES AND METHOD OF USE THEREOF

RELATED APPLICATION

The present application is a continuation of U.S. patent application Ser. No. 15/617,013, filed Jun. 8, 2017, which is a continuation of U.S. patent application Ser. No. 15/400,358, filed Jan. 6, 2017, which is a continuation of U.S. patent application Ser. No. 14/688,496, filed Apr. 16, 2015, which is a continuation of U.S. patent application Ser. No. 13/486,824, filed Jun. 1, 2012, which claims the benefit of and priority to U.S. provisional application Ser. No. 61/492,948, filed Jun. 3, 2011, the content of each of which is incorporated by reference herein in its entirety.

GOVERNMENT INTEREST

This invention was made with government support under CHE0847205 awarded by the National Science Foundation. The government has certain rights in the invention.

FIELD OF THE INVENTION

The invention generally relates to enclosed desorption electrospray ionization probes, systems, and methods.

BACKGROUND

Analysis of chemical and biological compounds using mass spectrometry is typically done with a procedure that includes sample preparation, chromatographic separation and mass analysis. In the case of biological materials, tissue is obtained and analytes are extracted prior to separation and pre-concentration by chromatography and examination by on-line mass spectrometry. There is a need for systems and methods for directly analyzing analytes from a sample or from tissue that avoids complex sample preparation processes.

SUMMARY

The invention generally relates to systems and methods that allow direct analysis of analytes from biological samples. In certain aspects, the invention provides a source of DESI-active spray, in which a distal portion of the source is enclosed within a transfer member such that the DESI-active spray is produced within the transfer member. In certain embodiments, the DESI-active spray is generated by an electrospray device.

An exemplary transfer member is a catheter. However, any type of tubing may be used as a transfer member, and the specific dimensions (e.g., length, inner diameter, outer diameter, etc.) will depend on the application to be performed. In certain embodiments, the distal portion is sealed within the transfer member. In other embodiments, a distal portion of the transfer member is configured to interact with a surface. In particular embodiments, the surface is tissue. In other embodiments, a proximal portion of the transfer member is configured to interact with a mass analyzer. The mass analyzer may be a bench top mass spectrometer or a handheld mass spectrometer.

The DESI-active spray may be any spray typically used in connection with analysis by mass spectrometry. For application to a biological sample, the DESI-active spray should be a solvent that is compatible with tissue, particularly living tissue. An exemplary solvent is water. In certain embodiments, the DESI-active spray is produced without the use of an applied voltage.

Another aspect of the invention provides a system for analyzing a sample that includes a source of DESI-active spray, a transfer member, and a mass analyzer, in which the system is configured such that a distal portion of the source is enclosed within the transfer member such that the DESI-active spray is produced within the transfer member, and a proximal portion of the transfer member is operably coupled to the mass analyzer. Exemplary mass analyzers include mass analyzers of a quadrupole ion trap, a rectalinear ion trap, a cylindrical ion trap, a ion cyclotron resonance trap, an orbitrap, a time of flight, a Fourier Transform ion cyclotron resonance, and sector instruments.

Another aspect of the invention provides a method of analyzing a sample that involves directing DESI-active spray droplets that are enclosed within a transfer member onto a surface to interact with the surface and desorb an analyte from the surface and generate ions of the analyte, wherein the transfer member is in contact with the surface, transferring the ions through the transfer member and into a mass analyzer, and analyzing the ions in the mass analyzer.

Another aspect of the invention provides a method for desorbing and ionizing an analyte in a sample material involving directing DESI-active spray droplets onto a surface of a sample material to interact with the surface and desorb the analyte, wherein the DESI-active spray is generated without use of a voltage source. In certain embodiments, the surface is tissue. Another aspect of the invention provides a method for desorbing and ionizing an analyte in a sample material involving directing DESI-active spray droplets onto a surface of a sample material to interact with the surface and desorb the analyte, wherein the DESI-active spray is water. In certain embodiments, the surface is tissue.

Another aspect of the invention provides a method of analyzing a sample that involves directing DESI-active spray droplets that are enclosed within a transfer member onto a tissue to interact with the tissue and desorb an analyte from the tissue and generate ions of the analyte, in which the transfer member is in contact with the surface, the DESI active spray comprises water, and the DESI-active spray is generated without use of a voltage source, transferring the ions through the transfer member and into a mass analyzer, and analyzing the ions in the mass analyzer.

Another aspect of the invention provides a source of DESI-active spray and a porous protective member covering a distal end of the source. In certain embodiments, the protective member is a thin mesh. The mesh may be made out of any material, such as plastics or metals. In certain embodiments, the mesh is metal.

Another aspect of the invention provides a method of analyzing a tissue sample that involves directing DESI-active spray droplets through a protective member onto a tissue to interact with the tissue and desorb an analyte from the tissue and generate ions of the analyte, in which the DESI active spray includes water and the DESI-active spray is generated without use of a voltage source, transferring the ions through a transfer member and into a mass analyzer, and analyzing the ions in the mass analyzer.

BRIEF DESCRIPTION OF THE DRAWINGS

FIGS. 7a-b illustrate ion mass spectra of rat brain tissue cross-section. FIG. 7a is by using methanol/water (50/50) solvent, and FIG. 7b is pure water solvent. FIGS. 7a-b are both via a 15 cm 1/8" Tygon transmission tubing with nebulizing pressure 120 psi.

FIG. 9b shows a 4 m-long, 1/16" i.d. TYGON tubing (flexible tubing) was used to probe the white matter of rat brain tissue section. Gas pressure at the gas cylinder is operated at 180 psi. FIG. 9c shows white matter of rat brain tissue section that was probed.

FIG. 10a shows analysis with normal DESI (gas pressure=180 psi, gas flow rate=1.3 L/min, solvent flow rate=3 μL/min). FIG. 10b shows analysis with 4 m DESI probe (gas pressure=180 psi, gas flow rate=4.3 L/min, solvent flow rate=8 μL/min).

FIG. 11a shows normal DESI was compared with different flow rates. FIG. 11b shows the ratio of normal DESI signal was compared with different flow rates. FIG. 11c shows that a DESI probe was tested in its operating flow rate range. FIG. 11d shows the ratio of DESI probe signal was compared in its operating flow rate range.

FIGS. 12a-b show analysis of rat brain tissue section with normal DESI in regular condition and DESI probe in biocompatible condition. FIG. 12a shows normal DESI condition: 2 cm fused silica capillary, ~1 cm transmission, MeOH/H$_2$O (1:1) solvent, voltage=−4.5 kV, gas pressure=200 psi, gas flow rates=1.5 L/min. FIG. 12b shows DESI probe condition: 80 cm fused silica capillary, 4 m transmission, H$_2$O solvent, voltage=0V, gas pressure=200 psi, gas flow rates=5.2 L/min.

FIG. 13a shows a scheme of minimally destructive DESI probe where a diaphragm pump was connected to the back end of the tube. (Pure water solvent, non-voltage mode, 1 m-long 1/16" i.d. TYGON tubing (flexible tubing), gas pressure=160 psi, gas flow rates=3.8 L/min). FIG. 13b: The left picture was taken after the rat kidney was analyzed when the pump is on. The right picture was taken after the rat kidney was analyzed when the pump is off. FIG. 13c shows the mass spectrum that was obtained from the surface of fresh rat kidney when pump is on.

FIG. 14a is pump is off and FIG. 14b is pump is on.

DETAILED DESCRIPTION

Figure 1:
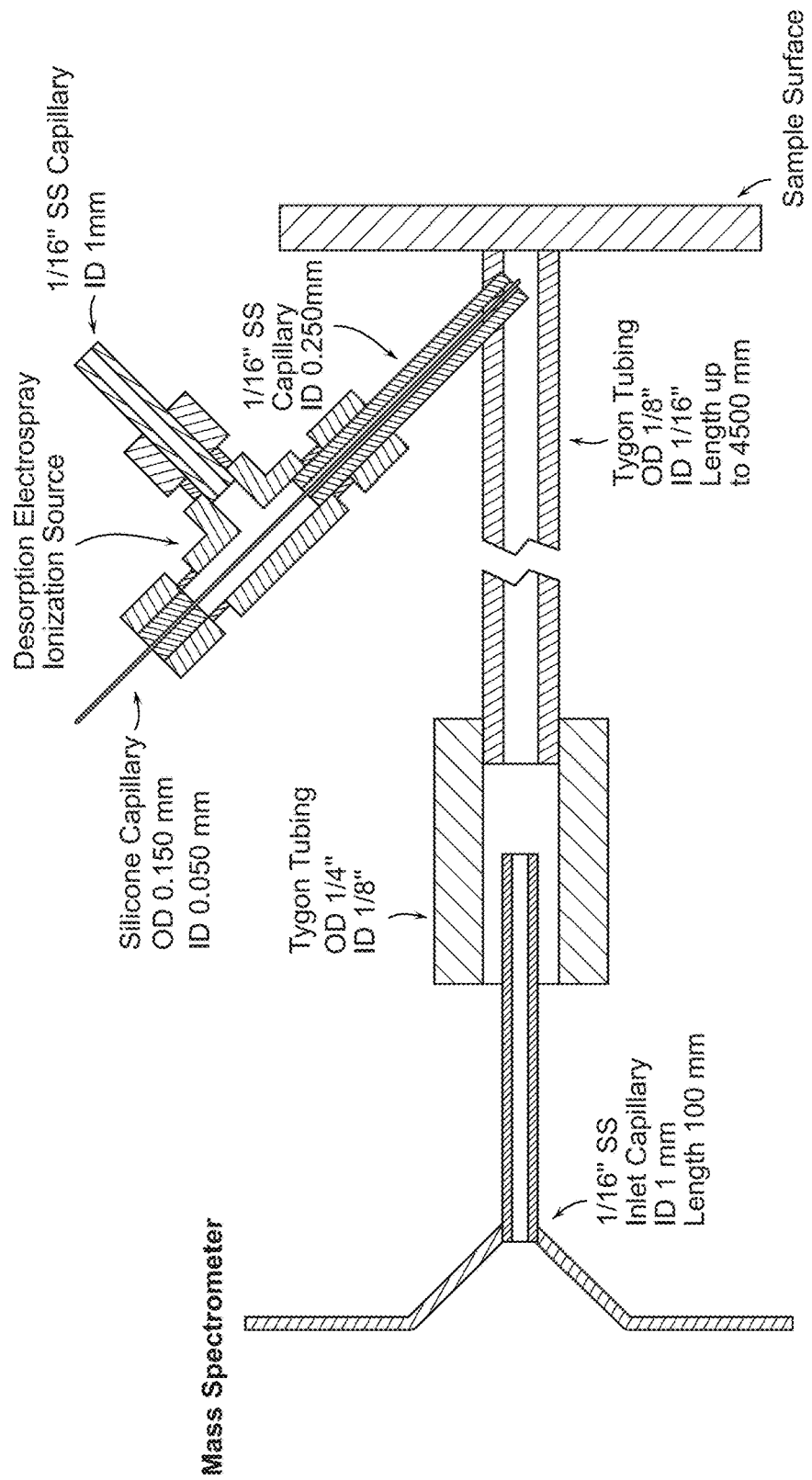
FIG. 1 is a schematic view of an enclosed DESI probe coupled with a mass spectrometer.

The invention generally relates to enclosed desorption electrospray ionization probes, systems, and methods. In certain embodiments, the invention provides a source of DESI-active spray, in which a distal portion of the source is enclosed within a transfer member such that the DESI-active spray is produced within the transfer member.

Desorption Electrospray Ionization (DESI)

DESI is an ambient ionization method that allows the direct ionization of analytes from surfaces, such as tissue (Takats et al., Science, 306:471-473, 2004 and Takats, U.S. Pat. No. 7,335,897, the content of each of which is incorporated by reference herein in its entirety). An exemplary DESI source is commercially available from Prosolia INC (Indianapolis, Ind. USA). Watrous et al. (*Journal of Mass Spectrometry*, 46(2):209-222, 2011) describes a DESI source and methods of constructing a DESI source. Generally, a DESI source may consist of an inner capillary (fused silica, 50 μm i.d., 150 μm o.d.) (Polymicro Technologies, AZ, USA) for delivering the spray solvent and an outer capillary (250 μm i.d., 350 μm o.d.) for delivering nitrogen nebulizing gas.

Ion Transfer

A typical prior art set-up that uses an ambient ionization source positions the ionization source about 2 cm or closer to the inlet of the ion analysis device. The transfer of the ion into the inlet of a mass spectrometer relies on the gas flow into the inlet under the influence of the vacuum of the spectrometer and the electric field in the surrounding area. The gas flow is typically low due to the low conductance of the inlet, which serve as the conductance barrier between atmosphere and vacuum manifold. Distances greater than 2 cm between the ionization source and the inlet of the ion analysis device result in diffusion of ions into the atmosphere and degradation of signal, i.e., inefficient or no transfer of ions into the ion analysis device.

Systems and methods of the invention generate a laminar gas flow that allows for efficient transfer of ions without significant loss of signal intensity over longer distances, such as distances of at least about 5 cm, at least about 10 cm, at least about 20 cm, at least about 50 cm, at least about 100 cm, at least about 500 cm, at least about 1 m, at least about 3 m, at least about 5 m, at least about 10 m, and other distances.

In aspects of the invention, the ion transfer member is operably coupled to the source of DESI-active spray and produces a laminar gas flow that transfers the gas phase ions to an inlet of the ion analysis device, such as a mass analyzer.

Systems of the invention provide enlarged flow to carry ions from a distant sample to an inlet of an ion analysis device, such as an inlet of a mass spectrometer. The basic principle used in the transport device is the use of the gas flow to direct gas and ions into the ion transfer member and to form a laminar flow inside the ion transfer member to keep the ions away from the walls while transferring the gas and ions through the ion transfer member. The analyte ions of interest are sampled at some point downstream along the ion transfer member. The laminar flow is achieved by balancing the incoming and outgoing gas flow. Thus recirculation regions and/or turbulence are avoided. Thus, the generated laminar flow allows for high efficient ion transport over long distance or for sampling of ions over large areas.

Systems of the invention also provide enlarged flow to carry ions from the ion source to an inlet of a miniature mass spectrometer, which has small pumping systems and compromised gas intake capability at the inlet. Additional gas flow provided by a miniature sample pump connected with the ion transfer member facilitates ion transfer from an ambient ionization source to the vicinity of the inlet of the miniature mass spectrometer. Thus the intensity of the ions for the analytes of interest is increased for mass analysis.

The ion transfer member, e.g., a tube with an inner diameter of about 10 mm or greater, is used to transfer ions from the ionization source to the inlet of an ion analysis device, e.g., a mass spectrometer. The larger opening of the ion transfer member, as compared to the opening of the inlet of the ion analysis device, is helpful for collection of sample ions generated in a large space, e.g. on a surface of large area. The large flow conductance of the ion transfer member allows the gas carrying ions to move toward the inlet of the ion analysis device at a fast flow rate. The ion transfer member is coupled to the DESI-active spray source such that a distal portion of the source is inserted within the transfer member so that the DESI-active spray is produced within the transfer member. The DESI-active spray source produces a gas flow inside the ion transfer member. The inlet of the ion analysis device receives the ions transferred from the ambient ionization source.

The ion transfer member may be any connector that allows for production of a laminar flow within it and facilitates transfer of ions without significant loss of ion current. Exemplary ion transfer members include tubes, capillaries, covered channels, open channels, and others. In a particular embodiment, the ion transfer member is a tube. The ion transfer member may be composed of rigid material, such as metal or glass, or may be composed of flexible material such as plastics, rubbers, or polymers. An exemplary flexible material is TYGON tubing.

The ion transfer member may be any shape as long the shape allows for the production of a flow to prevent the ions from reaching the internal surfaces of the ion transfer member where they might become neutral. For example, the ion transfer member may have the shape of a straight line. Alternatively, the ion transfer member may be curved or have multiple curves.

In still other embodiments, the ion transfer member includes additional features to prevent ions from being adsorbed onto the inside wall. For example, a dielectric barrier discharge (DBD) tubing is made from a double stranded speaker wire. The insulator of the wire serves as the dielectric barrier and the DBD occurs when high voltage AC is applied between the two strands of the wire. The DBD inside the tube prevents the ions from adsorbing onto the wall and provide a charge-enriched environment to keep the ions in the gas phase. This DBD tube can also be used for ionizing the gas samples while transferring the ions generated to the inlet of the ion analysis device. The DBD tube can also be used for ion reactions while transferring the ions generated to the inlet of the ion analysis device.

After moving through the ion transfer member, the ions are then separated based on their mass/charge ratio or their mobility or both their mass/charge ratio and mobility. For example, the ions can be accumulated in an ion analysis device such as a quadrupole ion trap (Paul trap), a cylindrical ion trap (Wells, J. M.; Badman, E. R.; Cooks, R. G., Anal. Chem., 1998, 70, 438-444), a linear ion trap (Schwartz, J. C.; Senko, M. W.; Syka, J. E. P., J. Am. Soc. Mass Spectrom, 2002, 13, 659-669), an ion cyclotron resonance (ICR) trap, an orbitrap (Hu et al., J. Mass. Spectrom., 40:430-433, 2005), a sector, or a time of flight mass spectrometer. Additional separation might be based on mobility using ion drift devices or the two processes can be integrated.

A sample can be from a mammal, e.g. a human tissue or body fluid. A tissue is a mass of connected cells and/or extracellular matrix material, e.g. skin tissue, nasal passage tissue, CNS tissue, neural tissue, eye tissue, liver tissue, kidney tissue, placental tissue, mammary gland tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, phlegm, saliva, sweat, amniotic fluid, mammary fluid, and cerebrospinal fluid (CSF), such as lumbar or ventricular CSF. A sample may also be a fine needle aspirate or biopsied tissue. A sample also may be media containing cells or biological material.

A sample can be from any surface with a distance from the mass spectrometer. The sample can be drug of abuse or explosives. The sampling and ionization occurs close to the surface while the generated ions are brought back to the mass spectrometer for analysis.

Incorporation By Reference

References and citations to other documents, such as patents, patent applications, patent publications, journals, books, papers, web contents, have been made throughout this disclosure. All such documents are hereby incorporated herein by reference in their entirety for all purposes.

Equivalents

The invention may be embodied in other specific forms without departing from the spirit or essential characteristics thereof. The foregoing embodiments are therefore to be considered in all respects illustrative rather than limiting on the invention described herein.

EXAMPLES

This invention generally relates to an ambient ionization probe that can be put through a catheter for in vivo sampling ionization of a biological sample and transfer of ions to a mass spectrometer for analysis. A sprayer is coupled with a long tubing (FIG. 1), of which the end can be pushed against a surface. The electrosprayed droplets impinge the surface, sampling the chemical compounds on the tissue. The nebulizing gas facilitates the collisions of the droplets with the surface, generates the secondary droplets and ions, and transfers the ions inside the tubing toward the mass spectrometer. Water, instead of solutions containing other solvents can be used as spray solvent for sampling the surface, which is friendly to the biological sample for in-vivo analysis. The long distance transfer of the droplets helps the desolvation of the droplets and the generation of the ions for MS analysis.

Example 1

System Setup

FIG. 1 is a schematic view of an enclosed DESI probe coupled with a mass spectrometer. The transmission tygon tubing (length 1.0-4.5 m) is sealed with the sample surface, including tissue cross-section and thin, allowing ions generated by desorption electrospray ionization (DESI) source to be vectored by the nebulizing gas flow. The counter side of tubing has a large diameter than the inlet capillary, avoiding the suction of exhaust gas into the mass spectrometer.

The sprayer is inserted into the transmission tubing. The spray outlet is about 3 mm away from the sample and almost vertical to the surface. The outer stainless steel tube carries Nitrogen as the nebulizing gas (O.D. 1/16", I.D. 0.250 mm). The inner fused-silica solvent capillary extends approximate 0.5 mm beyond the gas tubing with an O.D. of 0.150 mm and I.D. of 0.050 mm Methanol-water 50:50 (% vol/vol) is used as the solvent spray at a rate of 3 µL/min, while the nebulizing pressure ranges from 140 to 200 psi. The spray emitter can be redesigned and integrated with the long tubing for in-vivo analysis. The distance between the sprayer tip and the gas/solvent introduction port (Swagelok T in FIG. 1) can be extended and a fused silica capillary can be used to replace the stainless steel tubing to allow flexibility of the sprayer.

Figure 2A:
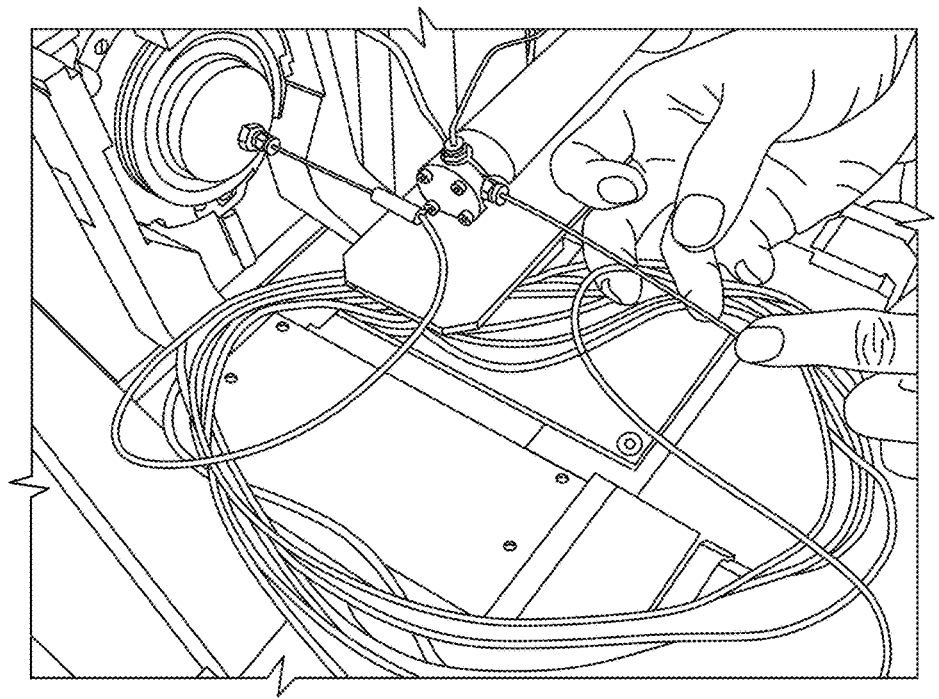
FIG. 2a is a photograph of an enclosed non-proximate DESI probe using 4.5 m 1/16" tygon transmission tubing combined with a commercial Thermo-Fisher mass spectrometer.
Figure 2B:
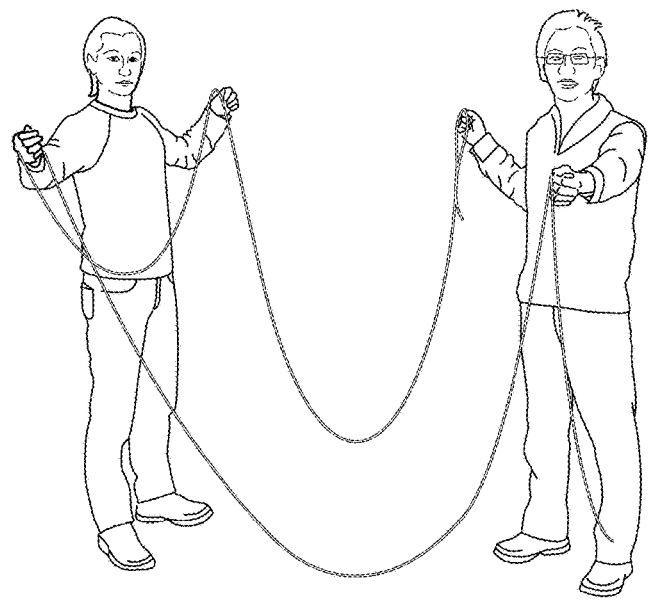
FIG. 2b is a photograph of the 4.5 m 1/16" tygon transmission tubing.
Figure 2C:
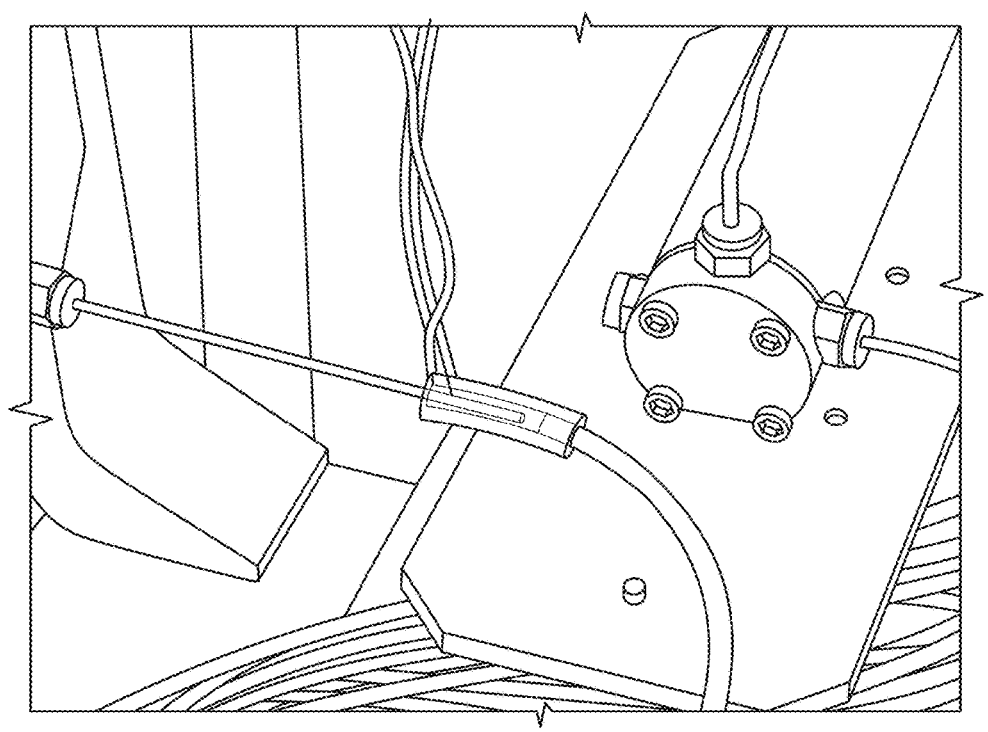
FIG. 2c is a photograph of the interface of 4.5 m 1/16" tygon transmission tubing and the mass spectrometer inlet.

FIG. 2a is a photograph of the thin detection by an enclosed non-proximate DESI probe using 4.5 m 1/16" tygon transmission tubing combined with a commercial Thermo-Fisher mass spectrometer. FIG. 2b is a photograph of the 4.5 m 1/16" tygon transmission tubing. FIG. 2c is a photograph of the interface of 4.5 m 1/16" tygon transmission tubing and the mass spectrometer inlet.

Example 2

Analysis of Tissue

Figure 3:
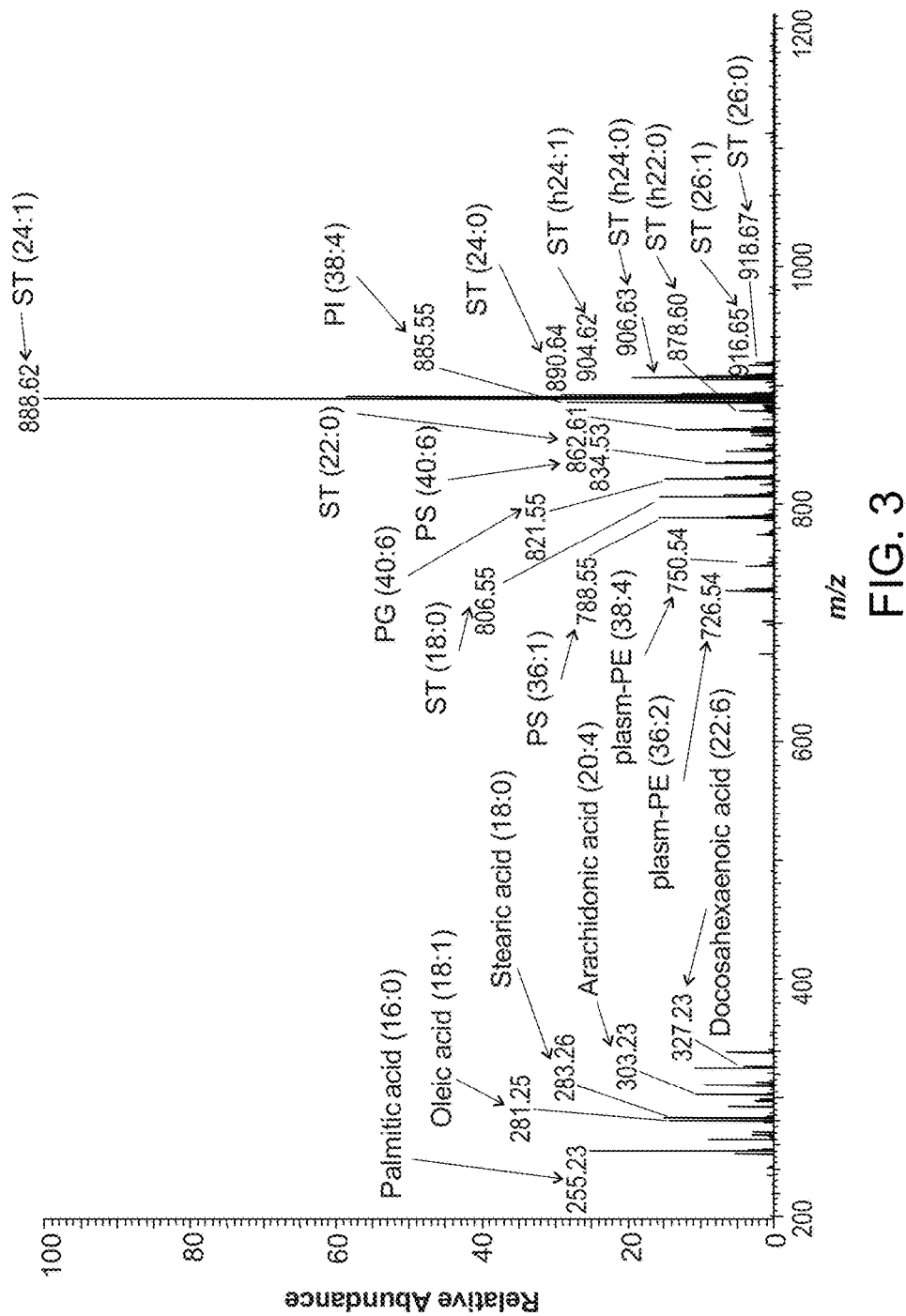
FIG. 3 is a typical negative ion mass spectrum of rat brain tissue cross-section using an enclosed DESI probe with 1.0 ml/16" tygon transmission tubing by a commercial Thermo-Fisher mass spectrometer.

FIG. 3 is a typical negative ion mass spectrum of rat brain tissue cross-section using an enclosed DESI probe with 1.0 ml/16" tygon transmission tubing by a commercial Thermo-Fisher mass spectrometer. The major ions observed in the low mass to charge region (m/z 200-400) correspond to deprotonated fatty acids including palmitic acid (16:0) m/z 255.23, oleic acid (18:1) m/z 281.25, stearic acid (18:0) m/z 283.26, arachidonic acid (20:4) m/z 303.23, and docosahexaenoic acid (22:6) m/z 327.23. In the high mass to charge region (m/z 700-1000), the major ions detected correspond to four main lipid classes: plasmenylglycerophosphoethanolamines(plasmenyl-PE), glycerophosphoserines (PS), glycerophosphoglycerols (PG), sulfatides (ST), and glycerophosphoinositols (PI). The (X:Y) behind each class represents the number of carbon atoms and number of double bonds in the fatty acid chains, respectively. The (hX:Y) means the lipid belongs to ahydroxylatedsulfatide species.

The parameters of the Orbitrap mass spectrometer was as following. Resolution: Enhanced (4 Hz); High voltage: ±4500 V; Capillary temperature: 275° C.; Capillary voltage: ±60 V; Tube lens voltage: ±145 V; Skimmer voltage: ±25; Maximum injection time: 250 ms; Number of microscans: 2; DESI nebulizing gas pressure: 160 psi. All the parameters are the same throughout the examples unless otherwise mentioned.

Example 3

Different Size Transfer Members

Figure 4:
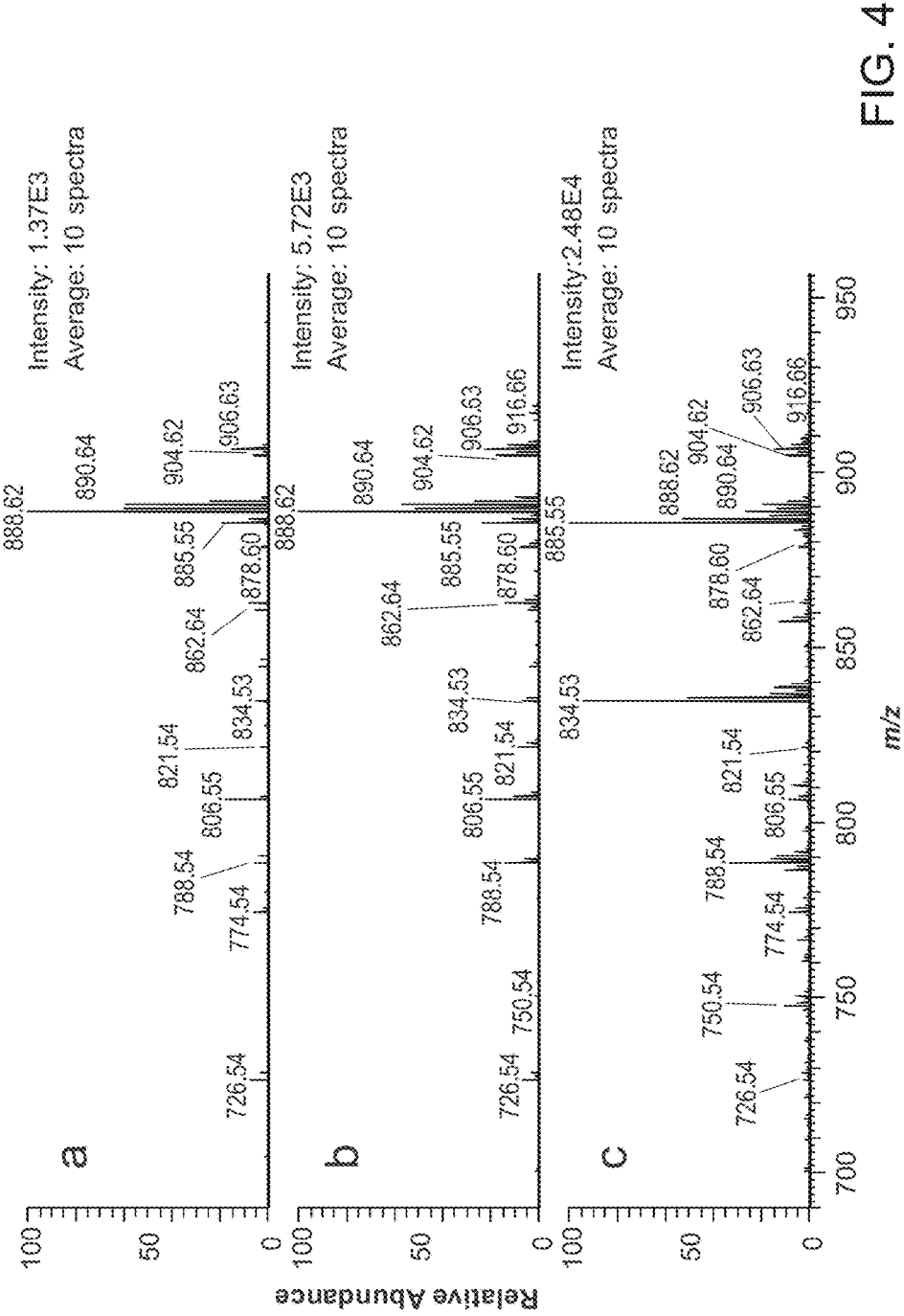
FIG. 4 shows negative ion mass spectra of the same rat brain tissue cross-section using (a) an enclosed DESI probe with 4.5 m 1/16" tygon transmission tubing (nebulizing gas pressure 200 psi), (b) an enclosed DESI probe with 1.0 m 1/16" tygon transmission tubing (nebulizing gas pressure 160 psi), and (c) a regular DESI (nebulizing gas pressure 140 psi) by the Orbitrap mass spectrometer.

FIG. 4 shows negative ion mass spectra of the same rat brain tissue cross-section using (a) an enclosed DESI probe with 4.5 m 1/16" tygon transmission tubing (nebulizing gas pressure 200 psi), (b) an enclosed DESI probe with 1.0 m 1/16" tygon transmission tubing (nebulizing gas pressure 160 psi), and (c) a regular DESI (nebulizing gas pressure 140 psi) by the Orbitrap mass spectrometer.

The main peaks in the mass spectra are corresponding to lipid including m/z 726.54 plasm-PE (36:2), m/z 750.54 plasm-PE (38:4), m/z 774.54 plasm-PE (40:6), mk788.54 PS (36:1), m/z 806.55 ST (18:0), m/z 821.54 PG (40:6), m/z 834.53 PS (40:6), m/z 862.64 ST (22:0), m/z 878.60 ST (h22:0), m/z 885.55 PI (38:4), m/z 888.62 ST (24:1), m/z 890.64 ST (24:0), m/z 904.62 ST (h24:1), m/z 906.63 ST (h24:0), and m/z 916.65 ST (26:1).

The relative abundance of the same lipid in each mass spectrum is different from each other mainly due to the different parts of the sample scanned, e.g. m/z 774.54 in FIG. 4b, m/z 834.53 and m/z 885.55 in FIG. 4c. Some peaks are missing because of the intensity drop with the increasing length of the transmission tubing, e.g. m/z 750.54 and 916.65 in FIG. 4a.

Regular DESI is carried out similar to the former paper (J. Am. Soc. Mass Spectrom. 2010, 21, 1177-1189). The distance from sprayer to sample is ~2 mm with an incident angle of ~45°. The inlet-to-sprayer distance is ~3 mm with a collection angle of 10°.

Example 4

Analyte Detection from a Surface

Figure 5:
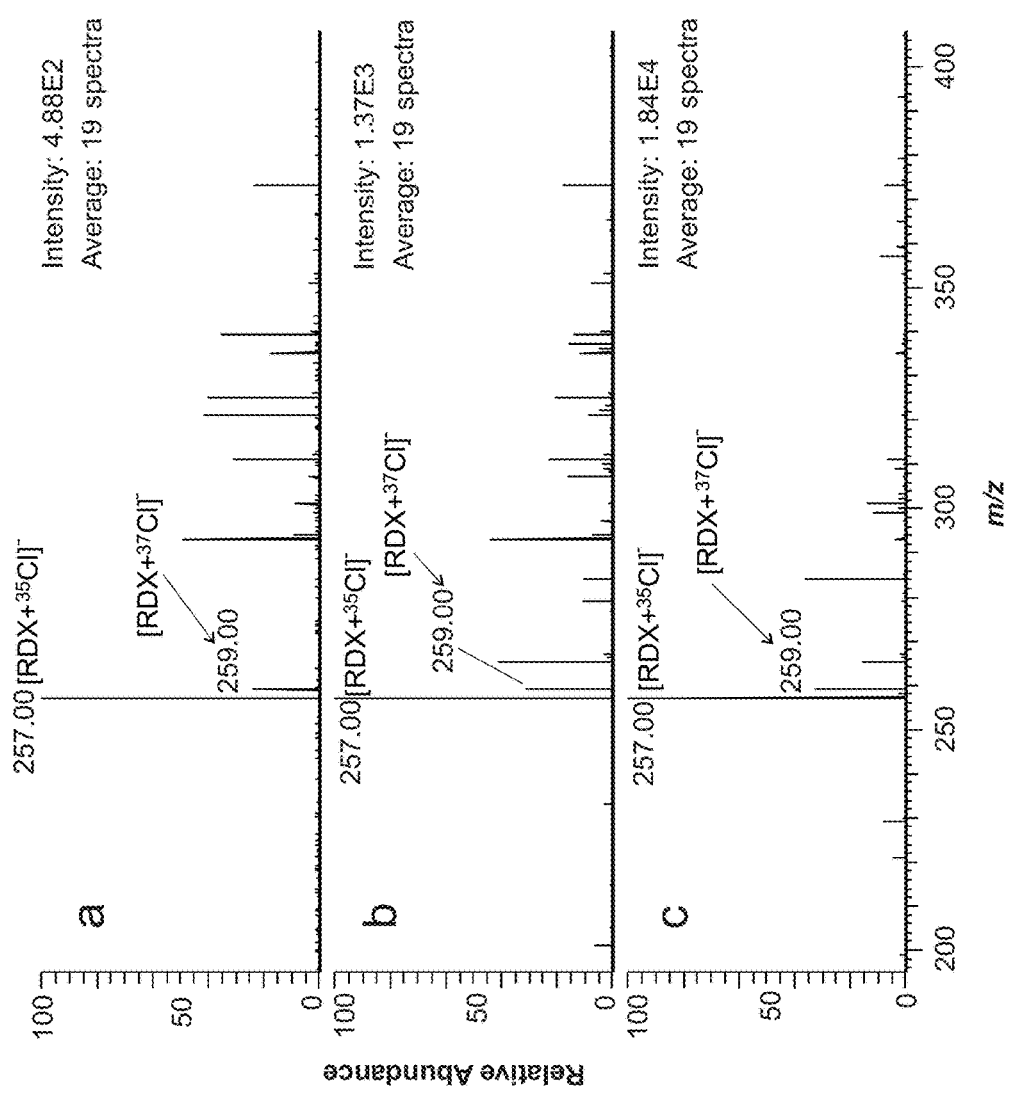
FIG. 5 demonstrates negative ion mass spectra of cyclotrimethylenetrinitramine (RDX) on glass slides using (a) an enclosed DESI probe with 4.5 m 1/16" tygon transmission tubing (5000 ngRDX deposited, nebulizing gas pressure 200 psi), (b) an enclosed DESI probe with 1.0 m 1/16" tygon transmission tubing (500 ng RDX deposited, nebulizing gas pressure 160 psi), and (c) a regular DESI (500 ng RDX deposited, nebulizing gas pressure 140 psi) by the Orbitrap mass spectrometer after background subtraction.

FIG. 5 demonstrates negative ion mass spectra of cyclotrimethylenetrinitramine (RDX) on glass slides using (a) an enclosed DESI probe with 4.5 m ¹⁄₁₆" tygon transmission tubing (5000 ng RDX deposited, nebulizing gas pressure 200 psi), (b) an enclosed DESI probe with 1.0 m ¹⁄₁₆" tygon transmission tubing (500 ng RDX deposited, nebulizing gas pressure 160 psi), and (c) a regular DESI (500 ng RDX deposited, nebulizing gas pressure 140 psi) by the Orbitrap mass spectrometer after background subtraction.

The major peak observed corresponds to the chloride adducts of RDX (RDX MW: 222.12 g/mol). The peak at m/z 257.00 is $[RDX+^{35}Cl]^-$ and the peak at m/z 259.00 is $[RDX+^{37}Cl]^-$. The parameters of regular DESI are the same as described in FIG. 4.

Example 5

Analyte Detection from a Tissue Surface

Figure 6:
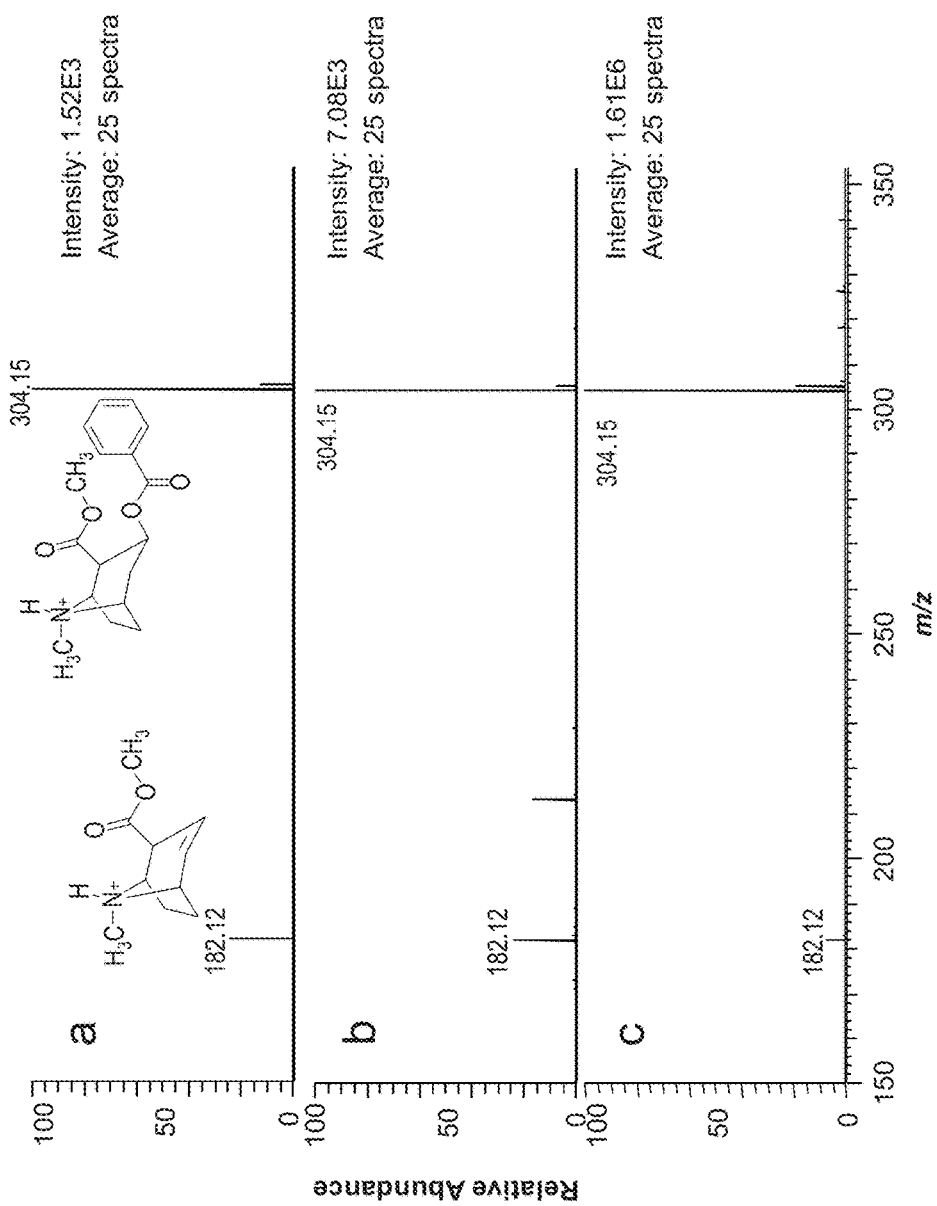
FIG. 6 illustrates positive ion mass spectra of 500 ng cocaine on finger using (a) an enclosed DESI probe with 4.5 m 1/16" tygon transmission tubing (nebulizing gas pressure 200 psi), (b) an enclosed DESI probe with 1.0 m 1/16" tygon transmission tubing (nebulizing gas pressure 160 psi), and (c) a regular DESI (nebulizing gas pressure 140 psi) by the Orbitrap mass spectrometer after background subtraction.

FIG. 6 illustrates positive ion mass spectra of 500 ng cocaine from a finger using (a) an enclosed DESI probe with 4.5 m ¹⁄₁₆" tygon transmission tubing (nebulizing gas pressure 200 psi), (b) an enclosed DESI probe with 1.0 m ¹⁄₁₆" tygon transmission tubing (nebulizing gas pressure 160 psi), and (c) a regular DESI (nebulizing gas pressure 140 psi) by the Orbitrap mass spectrometer after background subtraction.

The dominant peak observed is the protonated molecules of cocaine (MW: 303.353 g/mol) for each spectrum. The peak at m/z 182.12 is the fragment $[C_{10}H_{16}NO_2]^+$ by losing a molecule of benzoic acid. More fragments of m/z 182.12 were obtained when using the enclosed DESI probe compared to a regular DESI probe, but the intensity of the protonated molecules drops significantly at the same time. The parameters of regular DESI were the same as described in FIG. 4.

Example 6

DESI-spray Including Water

FIG. 7 illustrates ion mass spectra of rat brain tissue cross-section by using (a) methanol/water (50/50) solvent, and (b) pure water solvent via a 15 cm ⅛" TYGON transmission tubing (flexible tubing) with nebulizing pressure 120 psi.

Regular solvent for DESI tissue imaging mass spectrometry is methanol/water (50/50); however organic solvent such as methanol is not acceptable for in-vivo applications because of its toxicity. Herein, biocompatible pure water solvent demonstrates its similar performance as regular solvent.

Example 7

DESI-spray without Voltage

Figure 8:
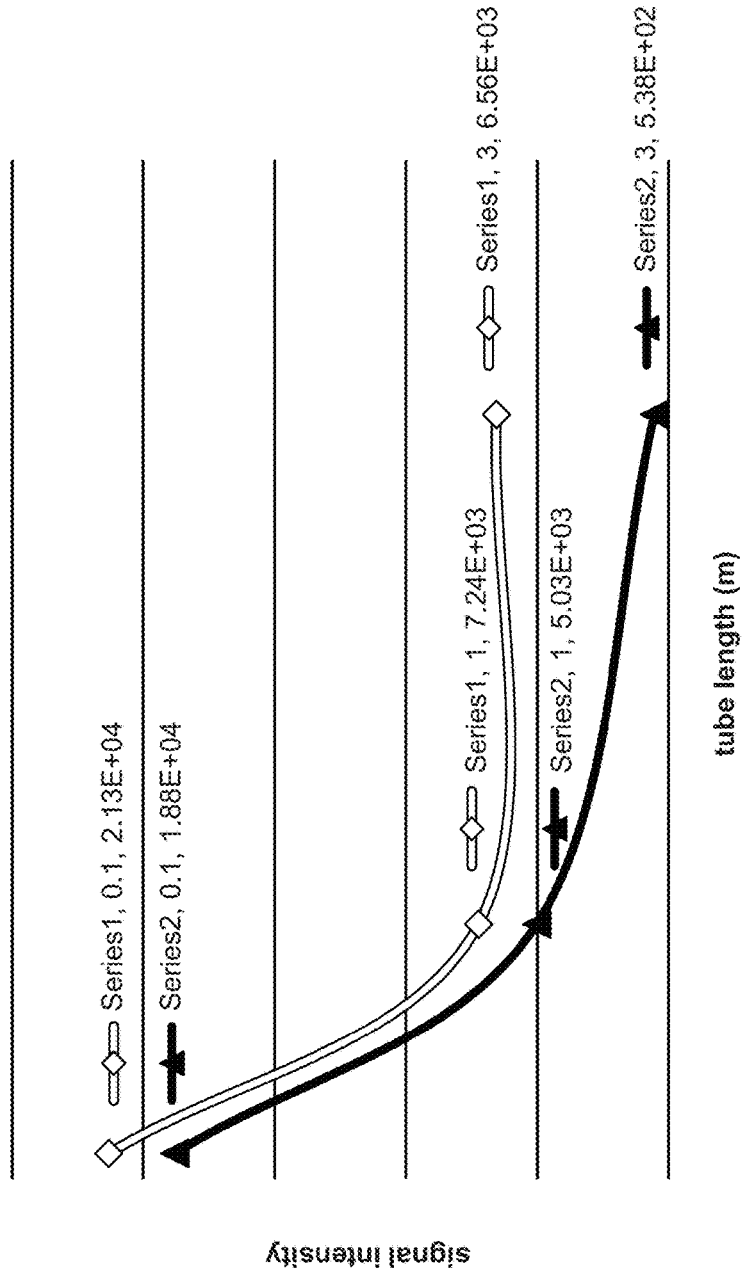
FIG. 8 illustrates ion mass spectra of 10 ng Pentachlorophenol on plastic slide by using −4.5 kV (blue curve) and 0V (red curve) with different length of 1/8" tube. When tube length is 1 m, the signal intensity of non-voltage DESI probe only drops a factor of 1.5. When the tube length is 3 m, the signal intensity of DESI probe drops a factor of 12.

FIG. 8 illustrates ion mass spectra of 10 ng Pentachlorophenol desorbed from a plastic slide by using −4.5 kV (blue curve) and 0V (red curve) with different length of ⅛" tube. When the tube length is 1 m, the signal intensity of non-voltage DESI probe only dropped a factor of 1.5. When the tube length was 3 m, the signal intensity of DESI probe dropped a factor of 12.

Data herein show that there was no significant difference between high voltage and no voltage in our DESI probe when the transmission tube length is less than 1 m.

Example 8

DESI Sampling without Damaging Tissue Sample

A thin mesh can be installed at the opening of the probe, in contact with or with a short distance to the tissue sample. The mesh can prevent mechanical damage to the tissue surface due to impinging by the gas flow and the droplets accelerated by the nebulizing gas. The sprayed solvent forms a thin liquid film that extracts the analytes from the tissue. The mesh is immersed in the liquid film and the secondary ions or droplet can be generated from the top of the mesh through the desorption electrospray.

Example 9

In Situ Analysis of an Intact Organ

A clinical desorption electrospray ionization (DESI) probe was designed here to perform real-time, in situ analysis on intact organs and it can be used for in vivo mass spectrometry. Analytes from the surface was picked up by the DESI charged droplets, and ions/charged droplets could be sent back to mass spectrometer via a long (e.g., up to about 4 m), thin (e.g., ¹⁄₁₆" i.d.), and flexible tube. Pure water was chosen as the spray solvent due to its biocompatibility, and higher signal intensity was obtained compared to pure methanol solvent. High voltage which is not suitable for in vivo analysis was removed from the spray source, and signal intensity didn't drop once DESI was operated in high gas-flow-rate region. There was no peak loss after a tissue section was analyzed with a 4 m-DESI probe (with pure water, without high voltage) compared to normal DESI. Less destruction was observed after an additional pump was added to the end of the tube. Besides less destruction, the probe could be gently touched to the organ and good sealing was provided. Finally, a clear lipid profile was obtained from the surface of a fresh intact rat kidney and no obvious wound was observed after the analysis.

a. Introduction

Mass spectrometry is distinguished in identifying a group of chemical compounds form a complex biological sample at one time. Routine procedures require extraction, sample preparation, and separation before mass analysis (Chace, D. H., Chem. Rev. 2001, 101, 445-477); ambient mass spectrometry provided an approach by directly analyzing biological sample (Cooks, R. G.; Ouyang, Z.; Takats, Z.; Wiseman, J. M., Science 2006, 311, 1566-1570). Tissue analysis by ambient mass spectrometry has been demonstrated its applications in the clinical field (Wiseman, J. M.; Puolitaival, S. M.; Takats, Z.; Cooks, R. G.; Caprioli, R. M., Angew. Chem.-Int. Edit. 2005, 44, 7094-7097; Nemes, P.; Woods, A. S.; Vertes, A., Anal. Chem. 2010, 82, 982-988; and Wang, H.; Manicke, N. E.; Yang, Q. A.; Zheng, L. X.; Shi, R. Y.; Cooks, R. G.; Zheng, O. Y., Anal. Chem. 2011, 83, 1197-1201).

A problem with this analytical technique is that tissue has to be taken out from the human body. Therefore, in vivo mass spectrometry which performs the analysis inside the body is shown herein to solve this problem. This probe is able to perform diagnosis inside the body; therefore, ions/charged droplets have to be transferred back to a distant mass spectrometer via a long, thin, and flexible tube. The biocompatibility of DESI including toxicity of spray solvent, risk of high voltage, and destruction of tissue were all considered in development of the probe described herein. Most solvents used in normal DESI are not suitable for in vivo analysis due to their toxicity; therefore, a nontoxic solvent should be applied. Herein, a pure water solvent was chosen for analysis and its performance was evaluated. Further, with probes of the invention, high voltage was removed from the spray source since it might cause potential risk during in vivo analysis. It was observed that the sensitivity of a DESI probe could be maintained in sufficiently high gas flow rates even after high voltage was removed.

It has been found that tissue damage from DESI was produced by high-velocity gas flow/droplets, which should be minimized during in vivo analysis. A new approach was proposed here by reducing DESI gas velocity toward the organ with another pumping flow in the opposite direction.

Finally, a clinical DESI probe was used for in-situ, real-time analysis of an intact organ. This mass spectrometric analysis applied pure water solvent, provided minimal destruction and operated without high voltage for spray ionization. Probes herein could be used, for example, to identify the cancer margin during the surgery or inserted into the biopsy channel of current endoscope to diagnose cancer.

b. Materials

Rat brain tissue section (thickness=10 μm) fixed on the glass side was used for analysis. 0.25-0.5 μg polar lipid extractions (*E. coli* polar lipid extract from Avanti polar lipids, Inc.) were deposited on the teflon slides for analysis. Intact rat kidneys were taken after the sacrifice of rat. Solvents used here were pure water (D.I. water), methanol/water (1:1) and pure methanol.

A modified DESI source was characterized as inserting a 80 cm-long coaxial fused silica capillary (inner solvent capillary 50 μm i.d., 150 μm o.d.; outer gas capillary 530 μm i.d., 700 μm o.d.) into the front end of a Tygon® tubing (R-3603, length=0.1~4 m, 1/16" i.d., 1/8" o.d.) (FIG. 1A). A larger inner diameter of gas capillary was used in the DESI probe compared to normal DESI; therefore, higher gas flow rates were obtained when compared to normal DESI with the same pressure at the nitrogen gas cylinder. The solvent flow rates were operated at 4-8 μL/min and the nitrogen pressures of the gas cylinder were operated in the range of 90 to 200 psi (gas flow rate=1.5~5.2 L/min). An Exactive Orbitrap mass spectrometer (Thermo Scientific Inc., San Jose, Calif.) was used for mass analysis. The original heated capillary was replaced by an extended capillary and it was heated to 275° C. A diaphragm pump (four-stage diaphragm pump N813.4 from KNF Inc., free flow rate=13 L/min) was connected to the back end of the Tygon® tubing when operating intact organ analysis. A vacuum guage (series 925C micropirani transducer) which offers a measurement range from $10^{-5}$ torr to atmosphere was used here to measure the pressures. Fluid dynamics was simulated with ANSYS.

c. Results

Figure 9A:
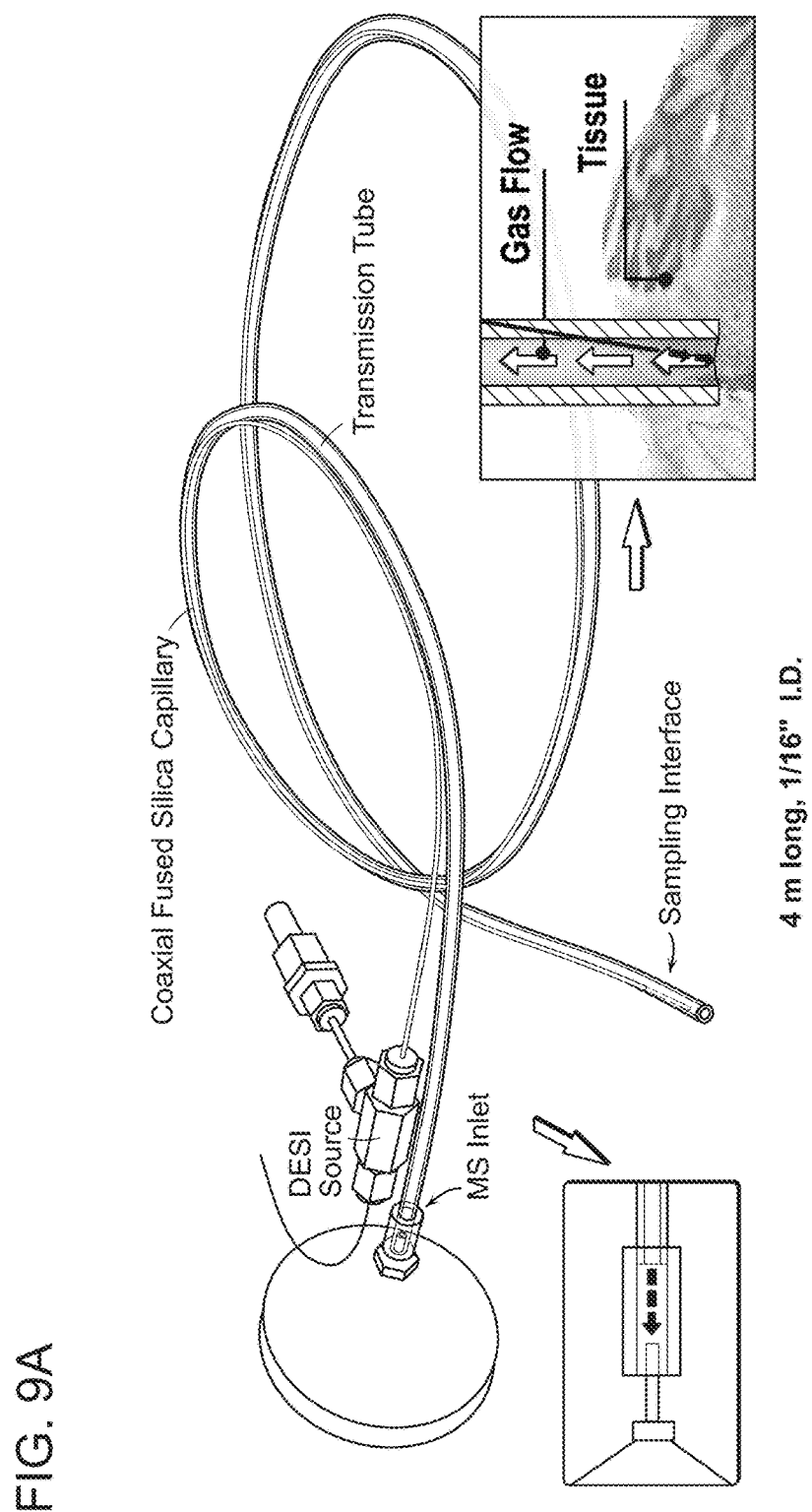
FIG. 9a is a schematic of a DESI probe which is composed of a coaxial fused silica capillary and an ion transferring tube. Analytes from the tissue can be picked up by the DESI droplets and ions/charged droplets can be transferred back to the mass spectrometer via a long, thin, and flexible tube. There is a sealing enclosure at the front end and a non-sealing connection at the back end.

The clinical DESI probe in this example was designed for in vivo analysis. The sealing enclosure was produced after the probe was pushed against the target. The analytes in the tissue were dissolved and picked up by the charged droplets from the DESI spray, and ions/charged droplets were then carried by the DESI gas flow back to the mass spectrometer. At the back end of the tube, a non-sealing design was used to protect the vacuum of mass spectrometer (FIG. 9A). Material of the tube played an important role for transmission of ions/charged droplets especially when the inner diameter of the tube was smaller. Grounded metal tube was good for ion transmission but the rigidness of the tube limited its application. Many nonconductive materials are flexible but only few of them can provide good ion transmission efficiency. One of the nonconductive materials, TYGON-3603 (flexible tubing), was chosen as the transferring tubing, and it also benefits from flexibility, softness, and chemical resistance (Garimella, S.; Xu, W.; Huang, G.; Harper, J. D.; Cooks, R. G.; Ouyang, Z., Journal of mass spectrometry: JMS 2012, 47, 201-7). Herein, a long (4 m) and thin (1/16" i.d.) TYGON tubing (flexible tubing) was used to detect the white (FIG. 9B) and gray matter (FIG. 9C) of a rat brain tissue section.

Clear mass spectra were observed even after 4 m transmission, showing that efficient collection and transport of ions/charged droplets with a proper material of tubing provided good quality of mass spectra for analysis. Further, both fatty acid and lipid profiles were observed from the gray matter and only the lipid profile was shown at some locations of white matter. This data show that the DESI probes herein had the ability to tell the distribution of fatty acids among the tissue and it was not disturbed by the background signal. In addition, the analyzing time of a single point was ~3 seconds and which should be acceptable for in-situ, real-time analysis.

Figure 10A:
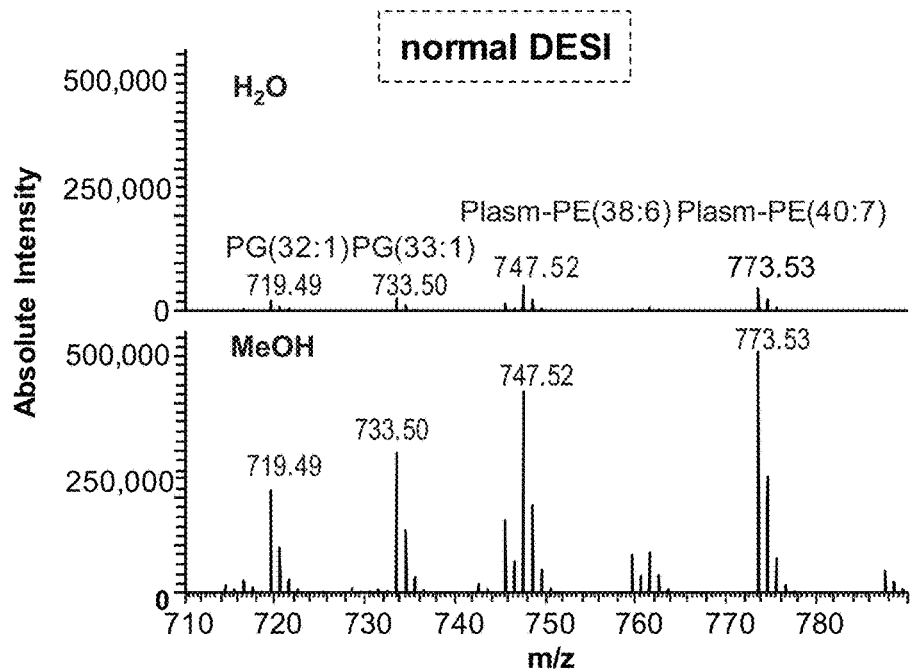
FIGS. 10a-b show a comparison between pure water solvent system and pure methanol solvent system by analyzing 0.5 μg extracted polar lipids deposited on the TEFLON (polytetrafluoroethylene) slides.
Figure 10B:
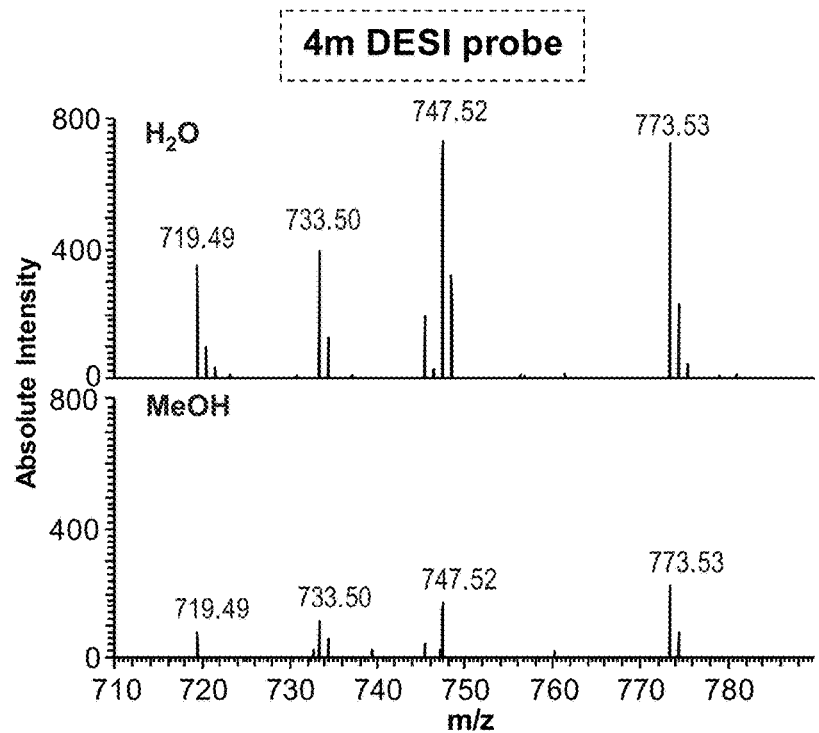
Figure 10C:
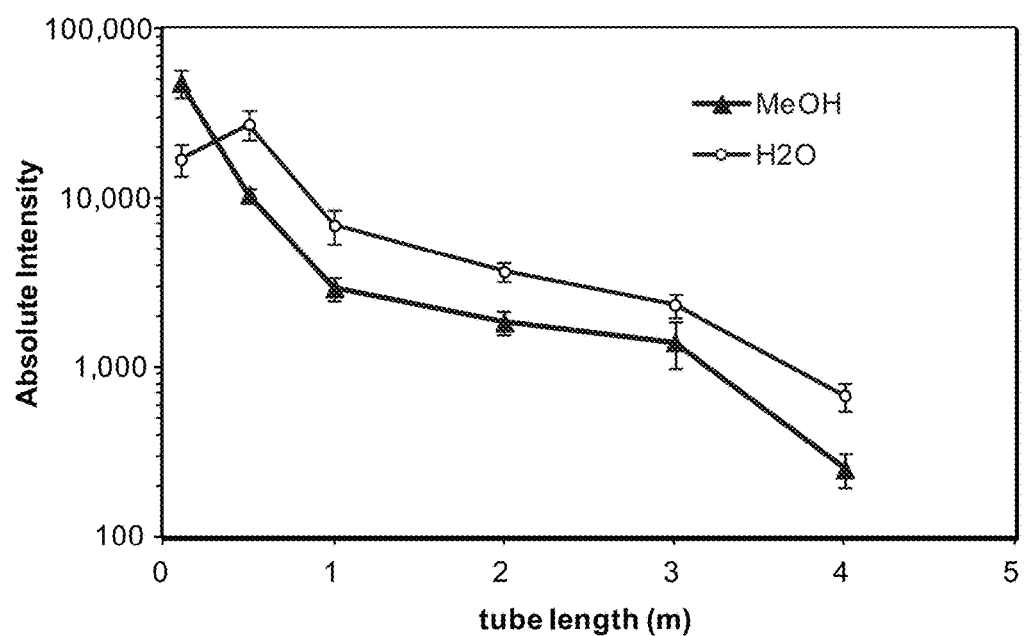
FIG. 10c shows different tube lengths ($0.1^{-4}$ m) that were compared with pure methanol and pure water solvent systems.

The solvent has to be changed for in vivo analysis since most organic solvents used in normal DESI are not biocompatible. Pure water was not preferred as a spray solvent in normal DESI since lower signal intensity was observed in most cases. The main cause is that pure water is more difficult for desolvation due to a higher boiling point and larger droplet size (due to larger surface tension) (Green, F. M.; Salter, T. L.; Gilmore, I. S.; Stokes, P.; O'Connor, G., Analyst 2010, 135, 731-737). Herein, pure water was chosen as the spray solvent due to its biocompatibility. The performance of pure water solvent (boiling point=100° C. at 1 atm; surface tension=72.86 mN/m at 20° C.) was evaluated here by comparing it with pure methanol solvent (boiling point=65° C. at 1 atm; surface tension=22.50 mN/m at 20° C.) both in the cases of normal DESI and DESI probe. It was observed that pure methanol provided 10 times higher signal intensity in the normal DESI (FIG. 10A); on the contrary, pure water provided 3 times higher signal intensity in the 4 m DESI probe (FIG. 10B). This similar trend also appeared in comparisons of different tube lengths (FIG. 10C). Pure methanol provided higher signal intensity at short distance (0.1 m) and pure water provided higher signal intensity at long distance (0.5~4 m). This data demonstrated that the sensitivity by using pure water was higher since the water droplets provided additional protection of ions during the transferring process.

Figure 11A:
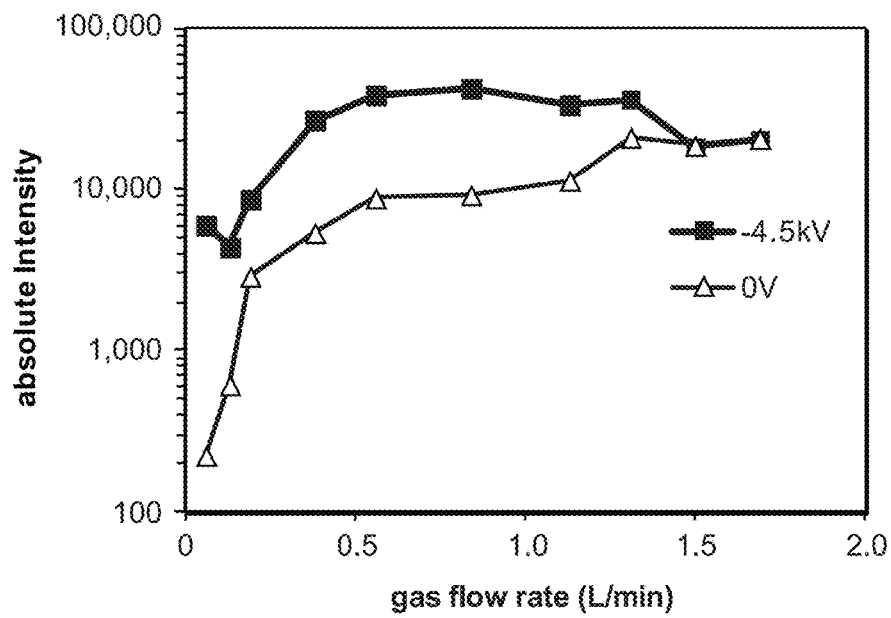
FIGS. 11a-d show comparisons between high-voltage mode and non-voltage mode in normal DESI and DESI probe.
Figure 11B:
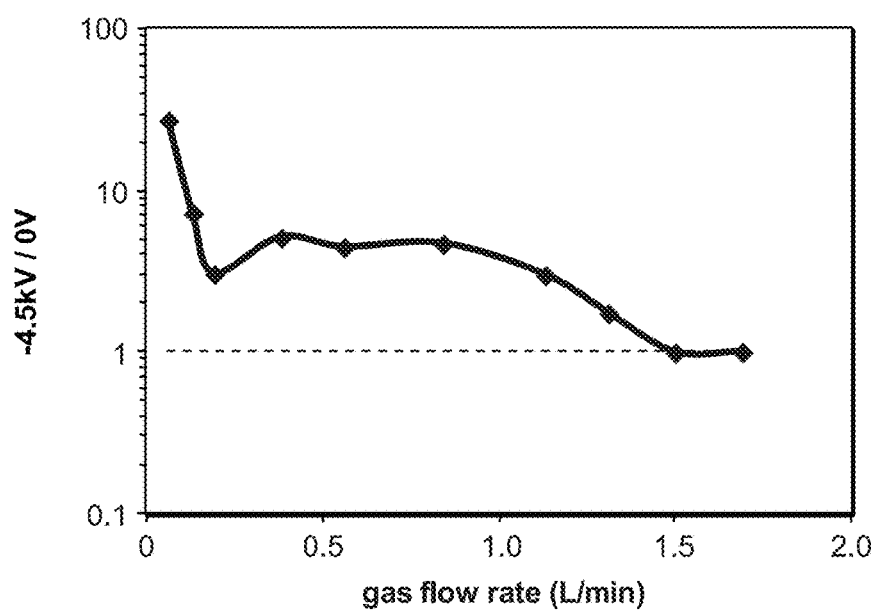
Figure 11C:
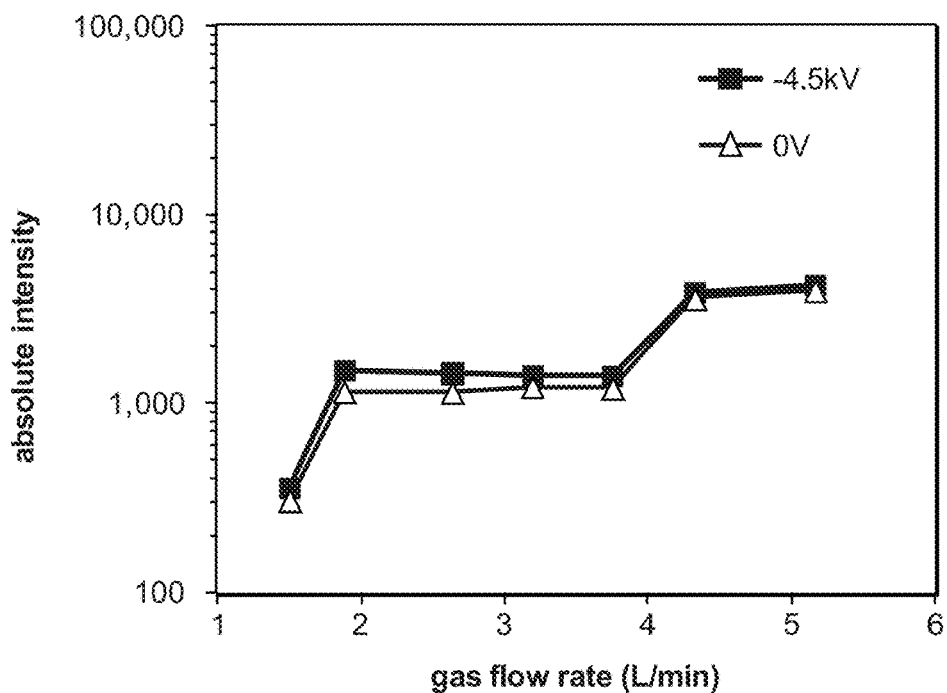
Figure 11D:
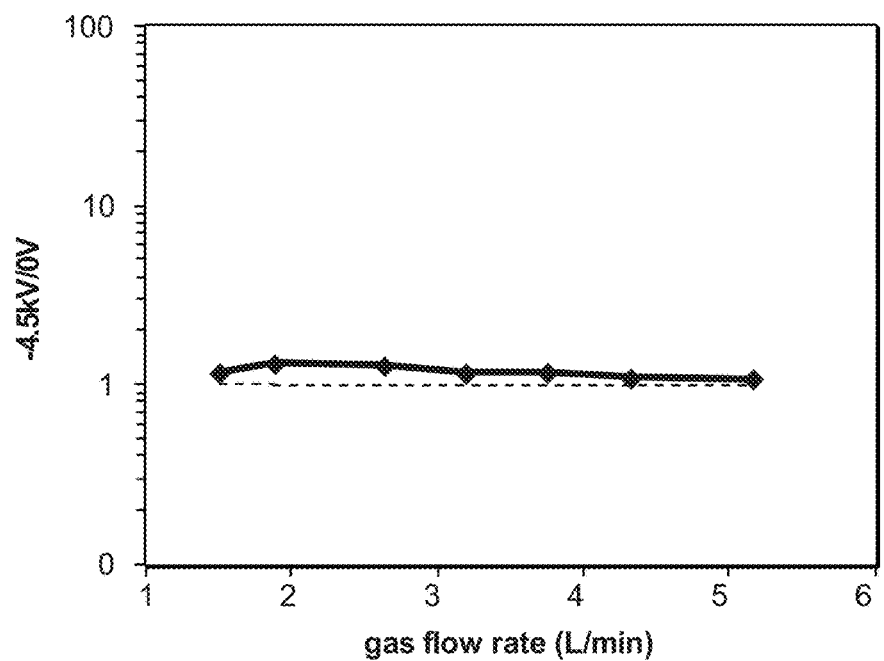

Normal DESI can operate both in high-voltage mode and non-voltage mode but generally the signal intensity is reduced once the high voltage is removed from the spray source (Ifa, D. R.; Wu, C. P.; Ouyang, Z.; Cooks, R. G., Analyst 2010, 135, 669-681; and Takats, Z.; Wiseman, J. M.; Cooks, R. G., J. Mass Spectrom. 2005, 40, 1261-1275). A wide range of gas flow rates (pressure=60-220 psi, flow rates=0.06-1.69 L/min) were tested in this Example. The results showed that high-voltage mode providing higher signal intensity only happens at a gas flow rate that is lower than 1.5 L/min (FIG. 11A). The signal intensity of non-voltage mode (0V) was closer to high-voltage mode when the gas flow rate was higher, and it was almost equal when the flow rate was higher than 1.5 L/min (FIG. 11B). The gas flow rates of the DESI probe were operated in the range of 1.5 and 5.2 L/min. It was observed that there was no significant difference between high-voltage mode and non-voltage mode (FIG. 11C) and the signal ratios were kept in this range of gas flow (FIG. 11D).

Without being limited by any particular theory or mechanism of action, it is believed that high voltage for normal DESI plays an important role in providing charges to the droplets such as electrospray, but the DESI gas flow for desorbing analytes on the surface will provide some proportion of sonic spray to DESI. Once the gas flow exceeds some critical value such as 1.5 L/min in this case, sonic spray will dominate most of the nebulization and ionization of DESI. At that moment, there was no significant difference between applying high voltage or not in terms of signal intensity. In the case of this DESI probe, there was no difference if the operating gas flow rate was higher than the critical gas flow rate. Thus the DESI probe can operate without high voltage and the signal intensity is reduced if the gas flow rate is higher than the critical gas flow rate.

A 4 m DESI probe with biocompatible adjustment (without high voltage, with pure water) were compared to the normal DESI on a stage (with high voltage, with methanol/water 1:1) by measuring a rat brain tissue section. It was found that identical lipids form normal DESI and 4 m DESI probe could be identified (FIG. 12). These data show that the ionization mechanism of the DESI probe herein was about the same as normal DESI.

Figure 13A:
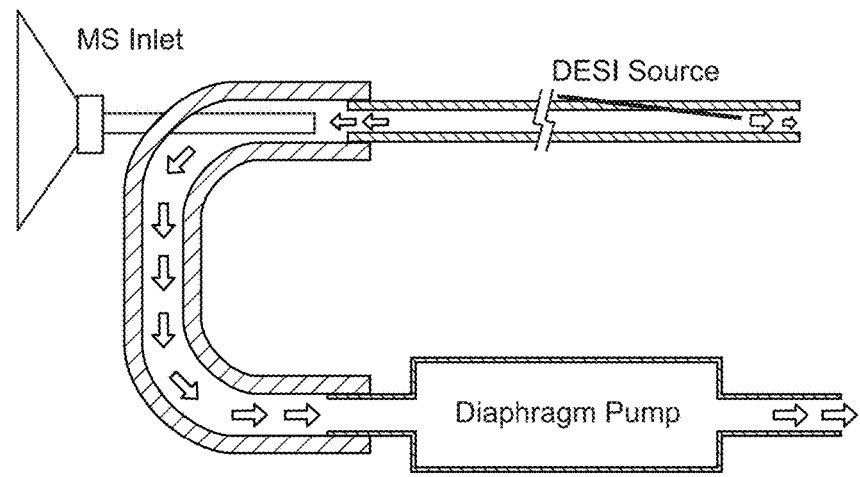
FIGS. 13a-c show that fresh rat kidney was measured with a minimally invasive DESI probe.
Figures 13D, 14A, 14B:
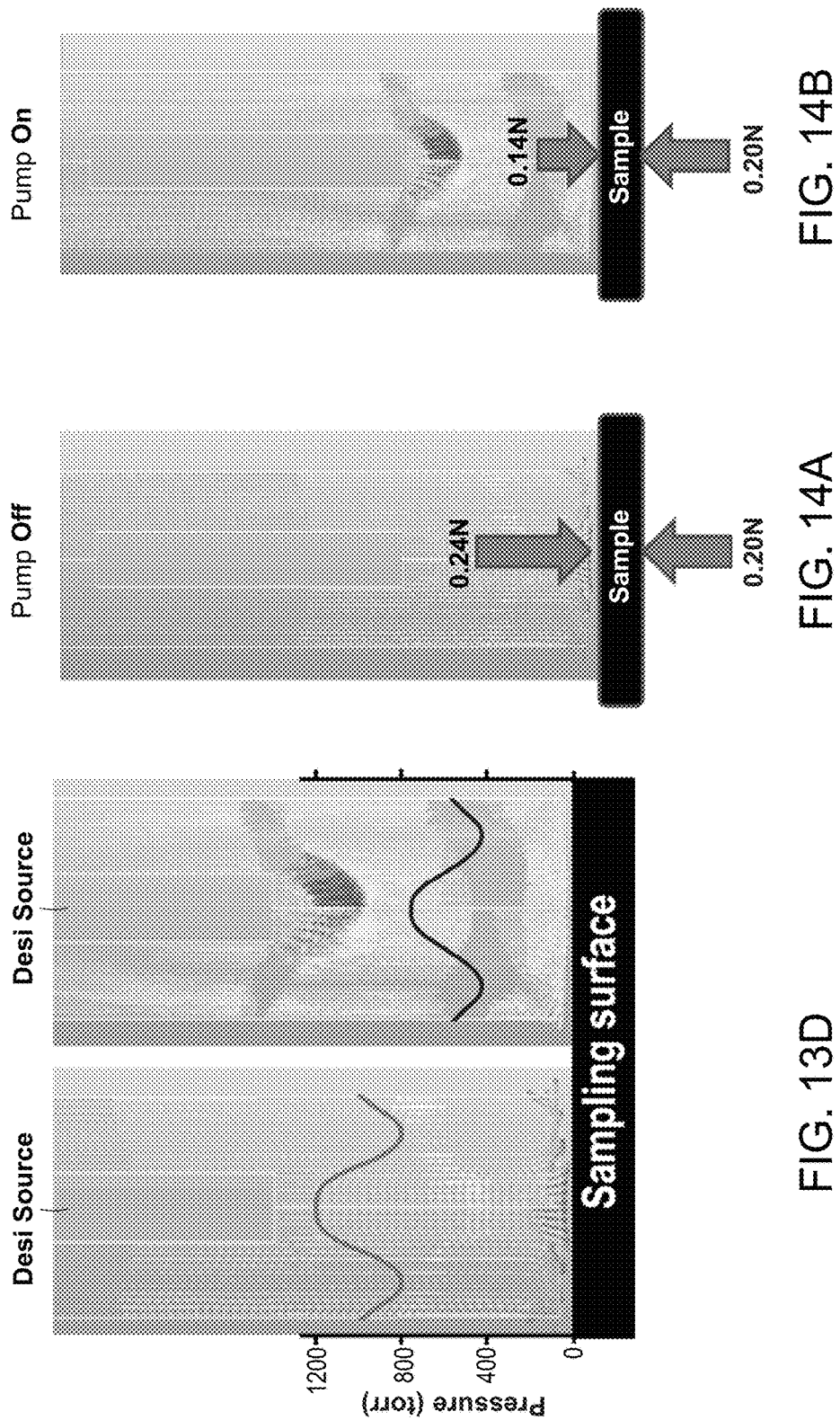
FIG. 13d shows that a comparison was made between pump is on and pump is off by using ANSYS fluid dynamics simulation. The front end of DESI probe consisting of a DESI source in the center of a TYGON tubing (flexible tubing) was shown here. Different colors indicate different pressures on the specific regions. Both pressures on the sampling surface were expressed on their corresponding diagrams.
FIGS. 14a-b are force diagrams of the sample via ANSYS simulation.

Optical approach dominates in vivo analysis due to its non-destructive ability. A large cause of destruction for DESI is the impact force from the high-velocity gas flow/droplets. The impact force can be reduced by lowering the gas flow rate from the DESI source, but the signal intensity will be reduced as well due to lower transmission and neubilization efficiency (FIG. 11C). It was determined that the best approach was reduction of the gas velocity toward the sampling surface while maintaining the gas velocity during nebulization and transmission. This was accomplished by reducing the gas velocity toward the organ by providing a pumping flow in the opposite direction; the pumping flow was provided by a diaphragm pump located at the back end of the tube (FIG. 13A). The velocity of DESI gas flow was reduced before it hit the organ; therefore, the impact force was reduced as well. A simulation was made here by comparing two situations, pump on and pump off, and it was observed that the pressure on the sampling surface was much reduced after the pump was turned on (FIG. 13D). It was observed that the impact force could be obtained by integrating the pressure on the sampling area.

Figure 13B:
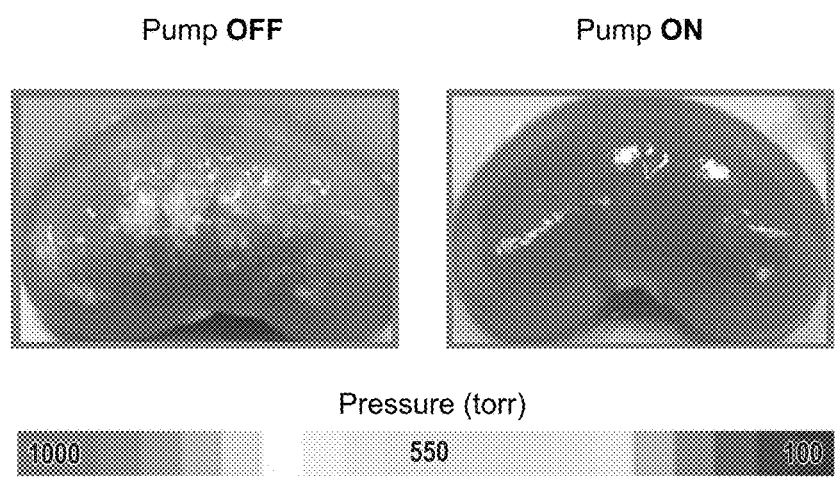
Figure 13C:
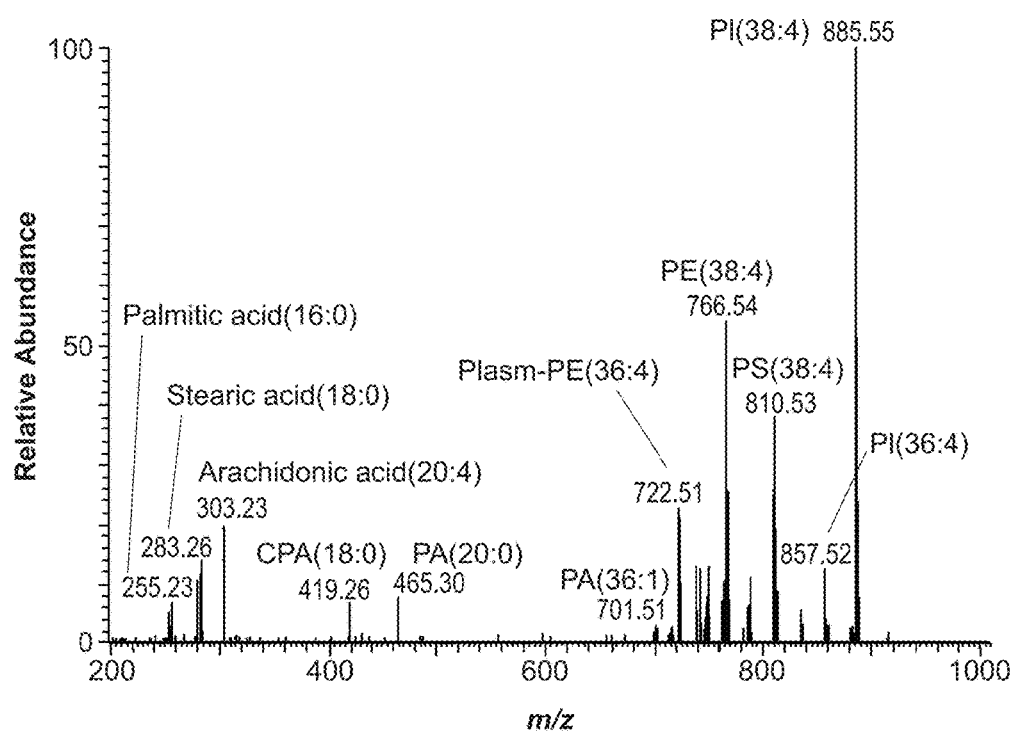

Fresh rat kidney was tested here, and it was found that no obvious wounds were observed when the pump was turned on (FIG. 13B), and a clear lipid profile was obtained (FIG. 13C). These results show that lipids on the surface of a kidney could be gently picked up by the DESI droplets after the impact force was reduced, demonstrating that living organ can be analyzed by mass spectrometry with minimal or no destruction. More specifically, lipids profiles were observed directly from the surface of organ; dissection was not always necessary. Another benefit of an additional pump was that a sealing enclosure could be produced only if the probe gently touched the organ (FIG. 14A). Without the pump, the probe has to be pushed against the surface to form a sealing enclosure (FIG. 14B). This provides an approach to gently form a sealing enclosure inside the body.

d. Conclusions

A clinical DESI probe was developed here and analytes on the surface of a fresh intact organ were analyzed in-situ. Pure water was chosen as spray solvent and it provided higher signal intensity due to droplets protection during transmission. High voltage was removed from the spray source and the sensitivity was kept at high gas flow rate. Minimal destruction was achieved by decreasing the gas velocity toward the organ via a pumping flow in the opposite direction. This clinical DESI probe was successfully applied to fresh intact organ analysis and all the process satisfied biocompatibility. Porbes herein may be used to analyze organs in living animals or the human body for disease diagnosis or basic medical research.

What is claimed is:

1. A method for analyzing a tissue section, the method comprising:
    providing a tissue section;
    directing a liquid droplet spray discharge from a desorption electrospray ionization probe onto the tissue section, wherein the liquid droplet spray discharge from the desorption electrospray ionization probe desorbs and ionizes an analyte from the tissue section in a manner that preserves the tissue section for further analysis;
    transferring the ions of the analyte to a mass spectrometer; and
    analyzing the ions of the analyte in the mass spectrometer, thereby analyzing the tissue section.

2. The method according to claim 1, wherein the method is repeated at least a second time on the same tissue section.

3. The method according to claim 1, wherein the discharge is water.

4. The method according to claim 1, wherein the desorption electrospray ionization probe operates without voltage.

5. The method according to claim 1, wherein the transferring step comprises sending the ions of the analyte through a transfer member that is operably coupled to the mass spectrometer.

6. The method according to claim 5, wherein the method further comprises generating a gas flow in the transfer member via a pump in a direction opposite that of a first direction with enough counter-flow to reduce a velocity of the discharge.

7. The method accordingly to claim 6, wherein a distal portion of the desorption electrospray ionization probe is sealed within the transfer member.

8. The method according to claim 7, wherein the distal portion of the transfer member is configured to sealably interact with the tissue section.

9. The method according to claim 1, wherein the mass spectrometer is a bench top mass spectrometer or a handheld mass spectrometer.

10. The method according to claim 1, wherein the tissue section is a brain tissue section.

11. A method for analyzing a tissue section, the method comprising:
    providing a tissue section;
    directing a liquid droplet spray discharge from a desorption electrospray ionization probe onto the tissue section, wherein the liquid droplet spray discharge from the desorption electrospray ionization probe desorbs and ionizes a lipid from the tissue section in a manner that preserves the tissue section for further analysis;
    transferring the ions of the lipid to a mass spectrometer; and
    analyzing the ions of the lipid in the mass spectrometer, thereby analyzing the tissue section.

12. The method according to claim 11, wherein the method is repeated at least a second time on the same tissue section.

13. The method according to claim 11, wherein the discharge is water.

14. The method according to claim 11, wherein the desorption electrospray ionization probe operates without voltage.

15. The method according to claim 11, wherein the transferring step comprises sending the ions of the analyte through a transfer member that is operably coupled to the mass spectrometer.

16. The method according to claim 15, wherein the method further comprises generating a gas flow in the transfer member via a pump in a direction opposite that of a first direction with enough counter-flow to reduce a velocity of the discharge.

17. The method accordingly to claim 16, wherein a distal portion of the desorption electrospray ionization probe is sealed within the transfer member.

18. The method according to claim 17, wherein the distal portion of the transfer member is configured to sealably interact with the tissue section.

19. The method according to claim 11, wherein the mass spectrometer is a bench top mass spectrometer or a handheld mass spectrometer.

20. The method according to claim 11, wherein the tissue section is a brain tissue section.

\* \* \* \* \*